(12) United States Patent
Albrecht et al.

(10) Patent No.: US 9,969,674 B2
(45) Date of Patent: May 15, 2018

(54) MMF-DERIVATIVES OF ETHYLENEGLYCOLS

(71) Applicant: RATIOPHARM GMBH, Ulm (DE)

(72) Inventors: Wolfgang Albrecht, Ulm (DE); Roland Selig, Ulm (DE); Frank Lehmann, Ulm (DE); Richard Guserle, Kötz (DE); Annemarie Maier, Biberach (DE)

(73) Assignee: ratiopharm GmbH, Ulm (DE)

( * ) Notice: Subject to any disclaimer, the term of this patent is extended or adjusted under 35 U.S.C. 154(b) by 0 days. days.

(21) Appl. No.: 15/303,939

(22) PCT Filed: Apr. 16, 2015

(86) PCT No.: PCT/EP2015/058257
§ 371 (c)(1),
(2) Date: Oct. 13, 2016

(87) PCT Pub. No.: WO2015/158817
PCT Pub. Date: Oct. 22, 2015

(65) Prior Publication Data
US 2017/0029357 A1 Feb. 2, 2017

(30) Foreign Application Priority Data

Apr. 17, 2014 (EP) .................................. 14165226
Jun. 26, 2014 (EP) .................................. 14174055

(51) Int. Cl.
*C07C 69/60* (2006.01)
*C07C 69/604* (2006.01)
*A61K 31/194* (2006.01)
*A61K 31/22* (2006.01)

(52) U.S. Cl.
CPC ............ *C07C 69/604* (2013.01); *C07C 69/60* (2013.01)

(58) Field of Classification Search
None
See application file for complete search history.

(56) References Cited

U.S. PATENT DOCUMENTS 2,415,366 A * 2/1947 Muskat .................. C08F 22/26
260/DIG. 28

OTHER PUBLICATIONS

PCT/EP2015/058257, Int'l Preliminary Report on Patentability & Written Opinon of the ISA, Oct. 18, 2016.
PCT/EP2015/058257, Int'l Search Report, Jun. 12, 2015.

* cited by examiner

*Primary Examiner* — Michael Barker
(74) *Attorney, Agent, or Firm* — Milstein Zhang & Wu LLC

(57) ABSTRACT

The present invention relates to novel compounds, e.g. for use as a medicament. In particular, the present invention relates to novel prodrugs of monomethyl fumarate (MMF) suitable as a medicament, preferably in the treatment and/or prevention of systemic diseases, autoimmune diseases, inflammatory diseases, for example multiple sclerosis, rheumatoid arthritis and psoriasis.

17 Claims, 12 Drawing Sheets

MMF-DERIVATIVES OF ETHYLENEGLYCOLS

Figure 1:
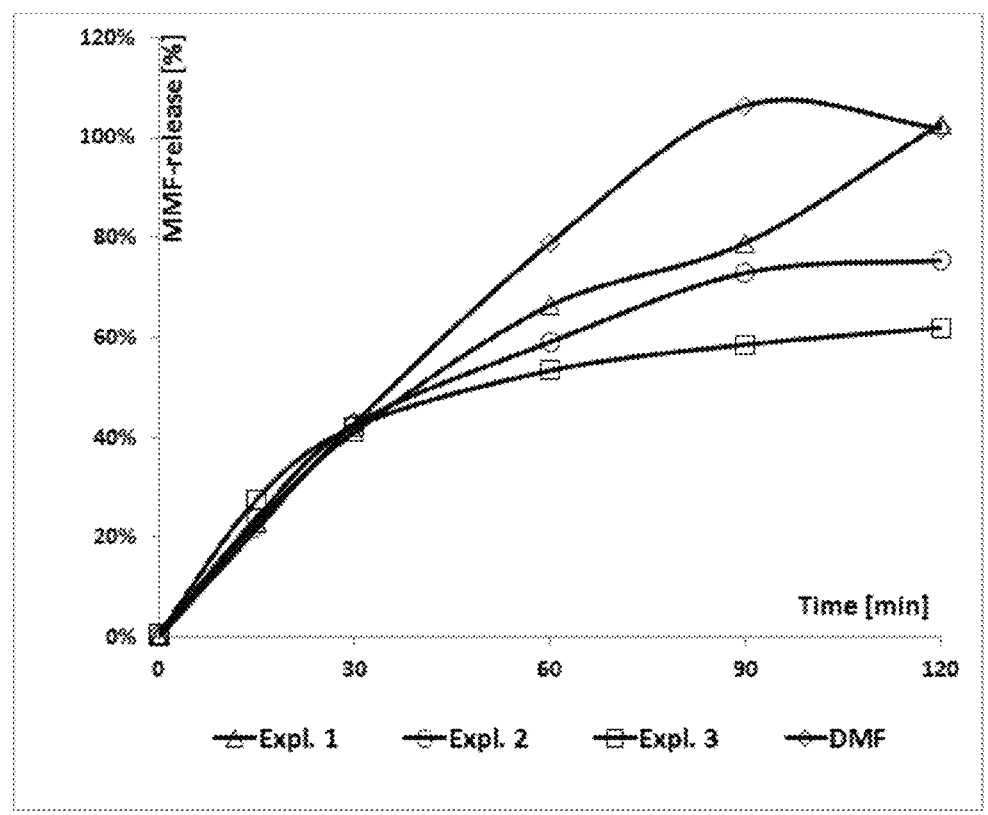

The present invention relates to novel compounds, e.g. for use as a medicament. In particular, the present invention relates to novel prodrugs of monomethyl fumarate (MMF) suitable as a medicament, preferably in the treatment and/or prevention of systemic diseases, autoimmune diseases, and/or inflammatory diseases, for example multiple sclerosis and psoriasis. Further, the invention relates to a pharmaceutical composition comprising the novel compounds.

BACKGROUND OF THE INVENTION

Dimethyl fumarate (DMF) is an oral therapeutic agent which is reported to reduce the rejection often occurring in connection with an organ transplantation (host versus graft reaction). Further, DMF is approved to be suitable as medicament for the treatment or prevention of a variety of diseases. For example, DMF is proposed in the treatment of autoimmune diseases such as multiple sclerosis. Further, DMF is suggested to be a suitable active pharmaceutical agent in the treatment of psoriasis. DMF is characterized by the following chemical Formula (1):

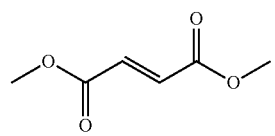

Formula (1)

When taken orally DMF is reported to be hydrolyzed for example by esterases in the intestine to monomethyl fumarate (MMF). MMF can be regarded as a metabolite of DMF and can be characterized by the following chemical Formula (2):

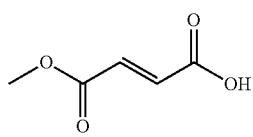

Formula (2)

The mechanisms of action of DMF or its metabolite MMF is reported to include inhibition of cytokine-induced nuclear translocation of the nuclear factor kappa B (NF-κB), apoptosis of stimulated T cells, and increased production of the $T_h2$ cytokines IL-4 and IL-5 in stimulated T cells, whereas generation of the $T_h1$ cytokine interferon gamma (IFN-γ) is supposed to remain unaffected. DMF is described to activate the transcription factor Nrf2 (nuclear factor erythroid 2-related factor 2), which binds to antioxidant response elements in the promoters of protective genes such as NADPH-quinone-oxidoreductase-1 (NQO1) and heme-oxygenase-1. Thus, this ultimately raises the levels of the important intracellular antioxidant glutathione (cf. Albrecht P. et al., Journal of Neuroinflammation 2012, 9:163).

Further, it is alleged that the treatment of animals or primary cultures of CNS cells with DMF or MMF resulted in increased nuclear levels of active Nrf2, with subsequent up-regulation of canonical antioxidant target genes. DMF or MMF treatment increased cellular redox potential, glutathione, ATP levels, and mitochondrial membrane potential in a concentration-dependent manner. Treating astrocytes or neurons with DMF or MMF also significantly improved cell viability after toxic oxidative challenge in a concentration-dependent manner. This effect on viability was lost in cells that had eliminated or reduced Nrf2. These data suggest that DMF and MMF are cytoprotective for neurons and astrocytes against oxidative stress-induced cellular injury and loss, potentially via up-regulation of an Nrf2-dependent antioxidant response. Thus, in summary, it is indicated that in vivo DMF and MMF show about the same the efficacy, in particular on the transcription factor Nrf2.

As mentioned above, when taken orally DMF is rather rapidly hydrolyzed by esterases in the intestine to monomethyl fumarate (MMF). Thus, significant amounts of MMF are released within a short period of time. Such a rapid hydrolysis in principle was expected to provide a high level of MMF in the plasma within a short period of time. However, it has been found that a high MMF plasma level might not be achievable. A reason might be that the organism might not be capable of transferring the complete amount of MMF to the sites of the body where the pharmacological action takes place.

Additionally, it is reported that DMF has to be administered in quite high amounts and that the pharmaceutically active agent often shows undesirable side effects such as flush and especially symptoms related to the gastrointestinal tract such as irritation of the stomach and diarrhea.

Consequently, there is still a need for new medicaments, preferably for use in the treatment and/or prevention of systemic diseases, autoimmune diseases, inflammatory diseases, for example multiple sclerosis, rheumatoid arthritis and psoriasis. The medicaments should be capable of being applied in appropriate doses and should not cause significant undesired side effects.

Hence, it was an object of the present invention to overcome the drawbacks of the above-mentioned market drug substance DMF.

It was an object to develop a compound to be used as a medicament for the above-mentioned diseases wherein said compound shows advantageous pharmacokinetic properties.

In particular, compounds should be provided which are hydrolysed differently to MMF, for example more rapidly or more slowly, especially more slowly than DMF in the human body (or under respective in-vitro conditions).

Further, the compounds should preferably cause few undesirable side effects.

Additionally, it was an object of the present invention to provide compounds which can be used in the treatment of an autoimmune disease, preferably the early phase of an autoimmune disease, in particular of multiple sclerosis, such that the progress of the disease can be delayed.

SUMMARY OF THE INVENTION

According to the present invention, the above objectives are achieved by the specific compounds described herein by Formula (I). Said compounds can be used as a medicament for the treatment and/or prevention of systemic diseases, autoimmune diseases, inflammatory diseases, for example multiple sclerosis, rheumatoid arthritis and psoriasis.

The compounds of the invention can be regarded as MMF prodrugs. Generally, a prodrug can be regarded as a substance that is administered to a subject (preferably human) in a pharmacologically inactive or pharmacologically less than fully active form, and is subsequently converted in the body of the subject to an active drug, preferably through metabolic processes occurring in the body of the subject. In other words, a prodrug usually serves as a type of 'precursor' to the intended drug.

Thus, the subject of the present invention is a compound according to Formula (I)

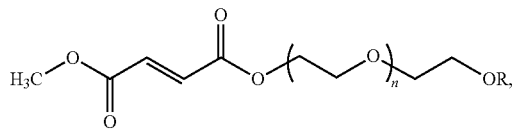

Formula (I)

wherein R is hydrogen and n is an integer of 1 to 10, or R is trans —CO—CH=CH—COOCH₃ and n is an integer from 2 to 10;
or a pharmaceutically acceptable salt, hydrate, solvate, polymorph, and/or mixtures thereof.

It was found that the compounds of the present invention show superior pharmaceutical and/or pharmacokinetic properties. In particular, the compounds show an advantageous hydrolyzation rate so that the lower dose of the compound can be applied to the patient.

Another subject of the invention is a compound according to Formula (I) wherein R is hydrogen or trans —CO—CH=CH—COOCH₃ and n is an integer of 0 to 10; or a pharmaceutically acceptable salt, hydrate, solvate, polymorph, and/or mixtures thereof for use as a medicament.

Further, the present invention relates to a compound according to Formula (I) wherein R is hydrogen or trans —CO—CH=CH—COOCH₃ and n is an integer of 0 to 10; or a pharmaceutically acceptable salt, hydrate, solvate, polymorph, and/or mixtures thereof for use in the treatment of systemic diseases, autoimmune diseases of inflammatory diseases like rheumatoid arthritis, preferably for use in the treatment of multiple sclerosis or psoriasis, in particular multiple sclerosis.

Another subject is a pharmaceutical composition comprising the above-mentioned compound according to Formula (I).

DETAILED DESCRIPTION OF THE INVENTION

In the context of this invention, the compound of the present invention is represented by the above Formula (I). Further, the compound may refer to pharmaceutically acceptable salts, hydrates, solvates, polymorphs and mixtures thereof. For example, the invention also refers to pharmaceutical acceptable salts of compounds according to Formula (I) or to solvates of salts or hydrates or polymorphs or the like. The same applies for all embodiments, e.g. for compounds of Formulae (II), (III), (VI) and (VII) as shown below.

The variable n is an integer from 1 to 10, preferably from 1 to 6, more preferably from 1 to 3.

It is particularly preferred that n is 1.
In an alternative particularly preferred embodiment n is 2.
In an alternative particularly preferred embodiment n is 3.
In a preferred embodiment n can be 4, 5, 6, 7, 8, 9 or 10.
R is hydrogen or trans —CO—CH=CH—COOCH₃.
In both alternatives n can be defined as above.
Preferably R can be hydrogen. A compound according to Formula (I) with R being hydrogen can be regarded as a (oligo)ethylene glycol wherein one of the hydroxy groups is esterified with MMF.

In a preferred embodiment of the invention in a compound according Formula (I) n is 1 and R is hydrogen.

In an alternative preferred embodiment of the invention in a compound according Formula (I) n is 2 and R is hydrogen.

In a further alternative preferred embodiment of the invention in a compound according Formula (I) n is 3 and R is hydrogen.

In a preferred embodiment of the invention in a compound according Formula (I) R is hydrogen and n is 4, 5, 6, 7, 8, 9 or 10.

Thus, in an especially preferred embodiment the compound according to Formula (I) is selected from the compounds according to Formulae (II), (III) and (IV)

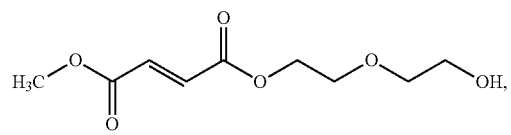

Formula (II)

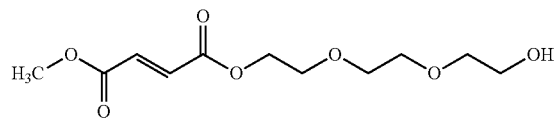

Formula (III)

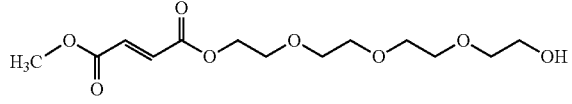

Formula (IV)

Alternative preferably R can be trans —CO—CH=CH—COOCH₃. A compound according to Formula (I) with R being trans —CO—CH=CH—COOCH₃ can be regarded as a (oligo)ethylene glycol wherein both of the hydroxy groups are esterified with MMF.

In a preferred embodiment of the invention in a compound according Formula (I) R is trans —CO—CH=CH—COOCH₃ and n is 4, 5, 6, 7, 8, 9 or 10.

In a particularly preferred embodiment of the invention in a compound according Formula (I) n is 2 and R is trans —CO—CH=CH—COOCH₃.

In an alternative particularly preferred embodiment of the invention in a compound according Formula (I) n is 3 and R is trans —CO—CH=CH—COOCH₃.

Thus, in an alternative especially preferred embodiment the compound according to Formula (I) is selected from the compounds according to Formulae (VI) and (VII)

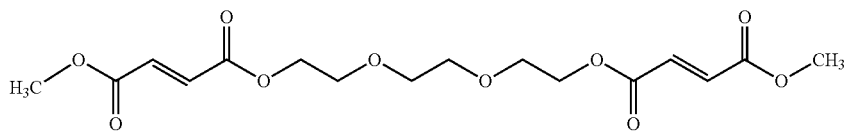

Formula (VI)

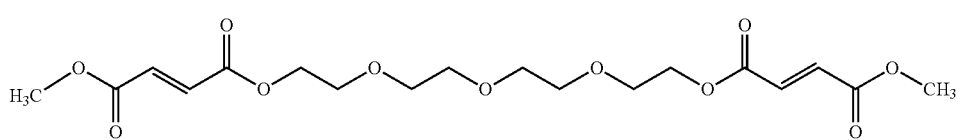

Formula (VII)

It is preferred that, in particular for non-medical use, a compound according to Formula (I) is not represented by a compound according to Formula (V)

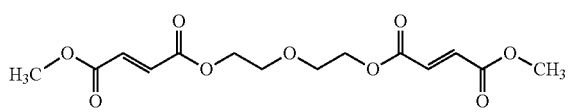

Formula (V)

A compound according to Formula (I) can preferably be synthesized via the following route:

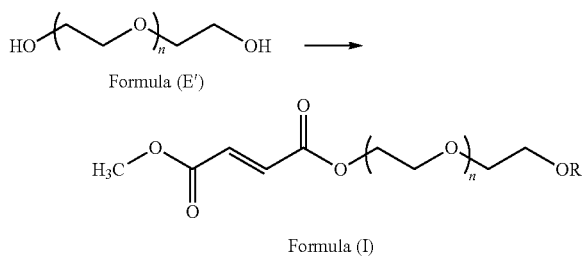

Preferably, in step a compound according to Formula (E') and MMF can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Suitable coupling agents can be for example DCC (N,N'-dicyclohexylcarbodiimide), DIC (N,N'-diisopropylcarbodiimide), EDC (N-ethyl-N'-(3-methylaminopropyl)carbodiimide hydrochloride), CDI (carbonyldiimidazole), preferably EDC. It is further preferred that the coupling reaction is carried out in the presence of an auxiliary alkaline compound. Suitable alkaline compounds are for example pyridine and amines, such as triethylamine, diisopropylethylamine and DMAP (4-(dimethylamino)pyridine), in particular DMAP.

A suitable organic solvent can for example be dichloromethane, chloroform, acetonitrile, dioxane, tetrahydrofuran and dimethylformamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with the compound according to Formula (E'), preferably in an organic solvent such as dioxane, tetrahydrofuran, chloroform or dichloromethane. Further, the reaction of the acid chloride with a compound according the compound according to Formula (E') is preferably carried out in the presence of an auxiliary alkaline compound. Suitable alkaline compounds are for example pyridine and amines, such as triethylamine, DMAP (4-(dimethylamino)pyridine and diisopropylethylamine, preferably triethylamine.

Alternatively, the above acid chloride of MMF can be further transferred in activated esters like the para-nitrophenol ester.

Further alternatively, MMF can be reacted with acid chlorides, diphenylphosphoryl azide or chlorosulfonyl isocyanate to form (mixed) anhydrides. These mixed anhydrides can be also submitted to further reactions to obtain further forms of anhydrides. For example, the anhydride of monomethylfumarate can be obtained by said preparation.

Subsequently, an activated ester or MMF anhydride can be submitted to a reaction with the compound according to Formula (E'), preferably in an organic solvent such as dioxane, tetrahydrofuran, chloroform, acetone or dichloromethane. Further, the reaction of an activated ester or MMF anhydride with the compound according to Formula (E') is preferably carried out in the presence of an auxiliary alkaline compound. Suitable alkaline compounds are for example pyridine and amines, such as triethylamine, diisopropylethylamine and DMAP (4-(dimethyl-amino)pyridine), preferably DMAP.

Alternatively, the reaction of the activated ester or MMF anhydride with the compound according to Formula (E') can preferably be carried out in the absence of an auxiliary alkaline compound.

A suitable organic solvent can for example be dioxane, tetrahydrofuran and dimethylformamide.

In a preferred embodiment one of the hydroxy groups of the compound according to Formula (E') can be protected with a protection group before being submitted to a reaction with MMF in the presence of a coupling agent or with the acid chloride of MMF or the anhydride of MMF. Such a protection group can for example be a trialkylsilyl group.

After the coupling reaction the protection can preferably be removed by a suitable reaction.

The above compounds according to Formula (I) show excellent pharmacokinetic properties. Within two hours the compounds show a hydrolysis into MMF and remaining organic residue wherein the hydrolysis is modified to the one of DMF. As a result, a smaller amount of MMF is released within the two hours and thus the compounds can be referred to as compounds (prodrugs of MMF) with an intrinsically retarded release of MMF. Additionally, the remaining organic residue is not expected to harm the patient's organism.

Further, the present invention relates to a compound according to Formula (I) wherein R is hydrogen or trans —CO—CH═CH—COOCH₃ and n is an integer of 0 to 10 or a pharmaceutically acceptable salt, hydrate, solvate, polymorph, and/or mixtures thereof for use as a medicament.

In a preferred embodiment in a compound of Formula (I) for use as a medicament n is an integer of 0 to 10, preferably of 1 to 6, and more preferably of 1 to 3, in particular 1, 2, or 3.

In a preferred embodiment n is 0, 4, 5, 6, 7, 8, 9 or 10.

It is particularly preferred that n is 1.

In an alternatively particularly preferred embodiment n is 2.

In an alternatively particularly preferred embodiment n is 3.

In a preferred embodiment in a compound of Formula (I) for use as a medicament R is hydrogen.

In a preferred embodiment of the invention in a compound according Formula (I) for use as a medicament R is hydrogen and n is 0, 4, 5, 6, 7, 8, 9 or 10.

In a particularly preferred embodiment of the invention in a compound according Formula (I) for use as a medicament n is 1 and R is hydrogen.

In an alternative particularly preferred embodiment of the invention in a compound according Formula (I) for use as a medicament n is 2 and R is hydrogen.

In a further alternative particularly preferred embodiment of the invention in a compound according Formula (I) for use as a medicament n is 3 and R is hydrogen.

In an especially preferred embodiment a compound according Formula (I) for use as a medicament is selected from the compounds according to Formulae (II), (III) and (IV)

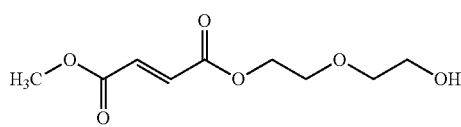

Formula (II)

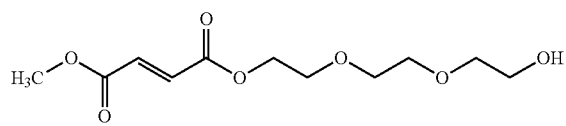

Formula (III)

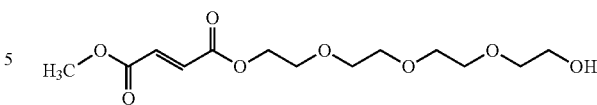

Formula (IV)

In an alternative preferred embodiment in a compound of Formula (I) for use as a medicament R is trans —CO—CH═CH—COOCH.

In a preferred embodiment of the invention in a compound according Formula (I) for use as a medicament R is trans —CO—CH═CH—COOCH and n is 0, 4, 5, 6, 7, 8, 9 or 10.

In a particularly preferred embodiment of the invention in a compound according Formula (I) for use as a medicament n is 1 and R is trans —CO—CH═CH—COOCH.

In an alternative particularly preferred embodiment of the invention in a compound according Formula (I) for use as a medicament n is 2 and R is trans —CO—CH═CH—COOCH.

In a further alternative particularly preferred embodiment of the invention in a compound according Formula (I) for use as a medicament n is 3 and R is trans —CO—CH═CH—COOCH.

In an especially preferred embodiment a compound according Formula (I) for use as a medicament is selected from the compounds according to Formulae (V), (VI) and (VII)

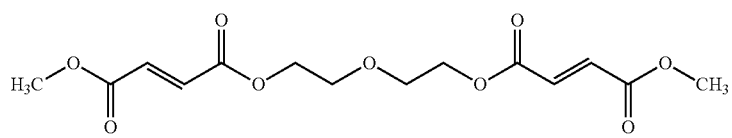

Formula (V)

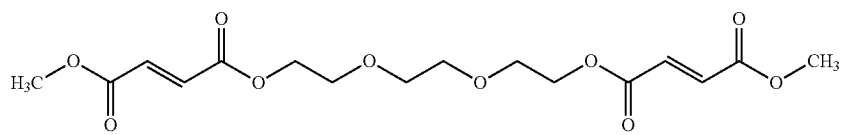

Formula (VI)

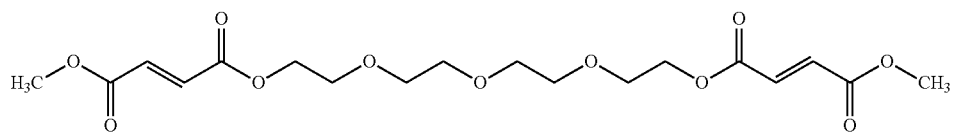

Formula (VII)

A further subject of the invention is a compound according to Formula (I) wherein R is hydrogen or trans —CO—CH═CH—COOCH₃ and n is an integer from 0 to 10 or a pharmaceutically acceptable salt, hydrate, solvate, polymorph, and/or mixtures thereof for use in the treatment and/or prevention of systemic diseases, autoimmune diseases or inflammatory diseases.

To an above compound according to Formula (I) for use in the treatment and/or prevention of systemic diseases, autoimmune diseases or inflammatory diseases the same applies as to a compound according to Formula (I) for use as a medicament.

Systemic diseases do not just affect single organs. Instead, these diseases are known to affect a number of organs and tissues or even the body as a whole.

People having an autoimmune disease usually suffer from their immune system mistakenly attacking their own cells of their organism and thus incorrectly responding to substances normally present in the body.

An inflammation can be defined as the response of the body to the occurrence of harmful stimuli which can result in pain, heat, redness, swelling and loss of function of the affected organ.

It is possible that some of the above-mentioned diseases cannot be allocated in one single group of the above-mentioned groups, since they show the symptoms of more than one of them.

In a further preferred embodiment, the above-mentioned compound according to Formula (I) is for use in the treatment of multiple sclerosis, rheumatoid arthritis and psoriasis, preferably multiple sclerosis. Said compounds can e.g. be used in the treatment of the following types of multiple sclerosis: relapsing-remitting, primary-progressive, secondary-progressive, and progressive-relapsing. In a preferred embodiment the compounds of the present invention are used in the treatment of relapsing-remitting multiple sclerosis.

Further, the present invention also provides a pharmaceutical composition comprising the compound according to the present invention, i.e. a pharmaceutical composition comprising a compound according to Formula (I) for use as a medicament and optionally pharmaceutical excipients.

In a preferred embodiment the pharmaceutical composition comprises
(i) 0.01 to 10 mmol, more preferably 0.05 to 5 mmol, still more preferably 0.25 to 3.5 mmol and particularly preferred 0.5 to 2.5 mmol of a compound according to Formula (I) for use as a medicament
(ii) pharmaceutical excipient(s).

In a further preferred embodiment the present composition can comprise one or more further excipients, preferably pharmaceutical excipients as described in the European Pharmacopoeia (Ph.Eur.) and/or in the US Pharmacopoeia (USP).

Examples of pharmaceutical excipients are carriers, binders, fillers, disintegrants, wicking agents, glidants and/or lubricants.

In a preferred embodiment the excipients are chosen such that the resulting formulation is a gastric juice-resistant formulation. In a preferred embodiment the formulation of the present invention does not show significant drug release under acidic conditions. In particular, the in-vitro drug release after 2 hours is less than 10%, preferably 0 to 9.9%, more preferably 0 to 5%, still more preferably 0.001 to 3%, measured according to USP, Apparatus II, paddle, 0.1 N HCl, 37° C., 50 rpm.

The pharmaceutical composition can be in a form suitable for oral administration, preferably in the form of a tablet or capsule, in particular in form of a tablet.

It is further preferred that the tablet is coated with a film coating. Alternatively, the capsule could also be coated.

In the present invention, the following three types of film coatings are possible:
film coating without affecting the release of the active ingredient,
gastric juice-resistant film coatings,
retard film coatings.

Generally, film coatings can be prepared by using film-forming agents such as waxes, cellulose derivatives, poly (meth)acrylate, polyvinylpyrrolidone, polyvinyl acetate phthalate, and/or shellac or natural rubbers such as carrageenan.

It is preferred that the present tablet is coated with a gastric juice-resistant film coating. Alternatively, a capsule comprising a gastric juice-resistant film coating can be used.

The gastric juice-resistant film coating preferably is a film coating being stable in the pH range of about 0.7 to 3.0, which is supposed to be the pH-value of human gastric juice found in the stomach. However, in an environment with a pH value of 5 to 9, which is supposed to be present in the (small) intestine of the human body, the gastric juice-resistant film coating preferably dissolves and the drug can be released.

The gastric juice-resistant film coating (often also referred to as enteric coating) can comprise film-forming agents being for example fats, fatty acids, waxes, alginates, shellac, polyvinyl acetate phthalate, cellulose derivatives such as carboxy methyl ethyl cellulose, cellulose acetate succinate, cellulose acetate phthalate, hydroxypropyl methyl cellulose phthalate, hydroxypropyl methyl cellulose acetate succinate, cellulose acetate trimellitate, and meth(acrylic)acid copolymers such as methyl acrylate-methacrylic acid copolymers, methyl methacrylate-methacrylic acid copolymers, Eudragits (for example Eudragit® L30D, Eudragit® L, Eudragit® S).

The coating is preferably free of active ingredient. It is further preferred that the thickness of the coating is usually 10 µm to 2 mm, preferably from 50 to 500 µm.

The preferred coating may comprise a film-forming agent and one or more of the following: lubricant, surfactant, glidant, pigment and water.

The preferred coating according to an embodiment of the present invention can comprise, along with the film-forming agent, e.g. stearic acid as lubricant for plasticizing and dissolving the polymer, sodium lauryl sulfate as a surfactant for wetting and dispersing, talc as glidant, iron oxide yellow and/or titanium oxide as pigment(s) and optionally purified water.

In a preferred embodiment the pharmaceutical composition can be administered one to three times a day, preferably once or twice a day, more preferably once a day.

Further, the present invention relates to a method for treating and/or preventing systemic diseases, autoimmune diseases and/or inflammatory diseases, preferably multiple sclerosis, rheumatoid arthritis or psoriasis, in particular multiple sclerosis, comprising administering to a subject in need thereof a therapeutically effective amount of the compound of the invention, in particular a compound according to Formula (I) where the residues are defined as above, or the pharmaceutical composition of the invention. To this compound and this pharmaceutical composition the same explanation (e.g. regarding combination of possible embodiments) apply as to the compound and the pharmaceutical composition as described above, respectively.

In a further aspect of the invention, the above objectives are achieved by the specific compounds described herein by Formula (I'). Said compounds can be used as a medicament for the treatment and/or prevention of systemic diseases, autoimmune diseases, inflammatory diseases, for example multiple sclerosis, rheumatoid arthritis and psoriasis.

The compounds of the invention can be regarded as MMF prodrugs. Generally, a prodrug can be regarded as a substance that is administered to a subject (preferably human) in a pharmacologically inactive or pharmacologically less than fully active form, and is subsequently converted in the body of the subject to an active drug, preferably through metabolic processes occurring in the body of the subject. In other words, a prodrug usually serves as a type of 'precursor' to the intended drug.

Thus, the subject of the present invention is a compound according to Formula (I')

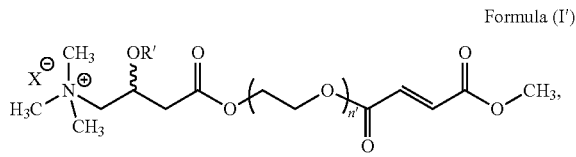

Formula (I')

wherein R' is hydrogen or —COCH₃,
n' is an integer from 1 to 10, and
X⁻ is a pharmaceutically acceptable anion,
or a hydrate, solvate, polymorph, and/or mixtures thereof.

It was found that the compounds of the present invention show superior pharmaceutical and/or pharmacokinetic properties. In particular, the compounds show an advantageous hydrolyzation rate so that an appropriate dose of the compound can be applied to the patient.

Another subject of the invention is a compound according to Formula (I') for use as a medicament.

Further, the present invention relates to a compound according to Formula (I') for use in the treatment of systemic diseases, autoimmune diseases of inflammatory diseases, preferably for use in the treatment of multiple sclerosis, rheumatoid arthritis or psoriasis, in particular multiple sclerosis.

Another subject is a pharmaceutical composition comprising the above-mentioned compound according to Formula (I').

In the context of this invention, the compounds of the present invention are represented by the above Formula (I'). Further, the compounds may refer to pharmaceutically acceptable hydrates, solvates, polymorphs and/or mixtures thereof. For example, the invention also refers to pharmaceutically acceptable solvates of the polymorphs or the like. The same applies to all embodiments, e.g. to compounds of Formulae (II') to (IX') as shown below. Further, the compounds according to Formula (I') can be in (R) or (S) configuration, preferably in (R) configuration.

X⁻ is a pharmaceutically acceptable anion. Examples of said anion are hydroxide, halogenides, such as fluoride, chloride, bromide, or iodide, nitrate, carbonate, hydrogen carbonate, sulphate, hydrogen sulphate, phosphate, monohydrogen phosphate, dihydrogen phosphate, and residues derived from organic acids, such as acetate, succinate, propionate, tartrate, oxalate, maleate, citrate, benzoate or lactate.

Generally, in Formula (I') the variable n' is an integer of 1 to 10 such as 1, 2, 3, 4, 5, 6, 7, 8, 9, or 10, preferably of 1 to 6, more preferably of 1 to 4. It is particularly preferred that n' is 1. In an alternative particularly preferred embodiment n' is 2. In an alternative particularly preferred embodiment n' is 3. In an alternative particularly preferred embodiment n' is 4.

Generally, in Formula (I') R' is hydrogen or —COCH₃.

Preferably R' can be hydrogen. A compound according to Formula (I') with R' being hydrogen can be regarded as an (oligo)ethylene glycol wherein one of the hydroxy groups is esterified with MMF and the other hydroxy group is esterified with carnitine.

In line with the present application carnitine refers to (R)-carnitine as well as to (S)-carnitine, preferably to (R)-carnitine.

In a preferred embodiment of the invention in a compound according Formula (I') n' is 1 and R' is hydrogen.

In an alternatively preferred embodiment of the invention in a compound according Formula (I') n' is 2 and R' is hydrogen.

In a further alternatively preferred embodiment of the invention in a compound according Formula (I') n' is 3 and R' is hydrogen.

In a further alternatively preferred embodiment of the invention in a compound according Formula (I') n' is 4 and R' is hydrogen.

Thus, in an especially preferred embodiment the compound according to Formula (I') is selected from the compounds according to Formulae (II'), (III'), (IV') and (V')

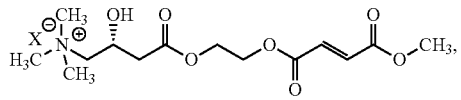

Formula (II')

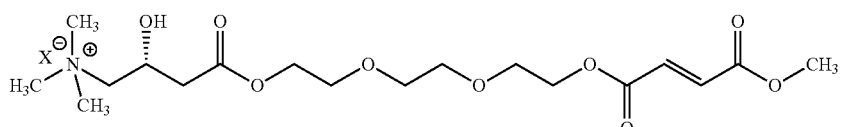

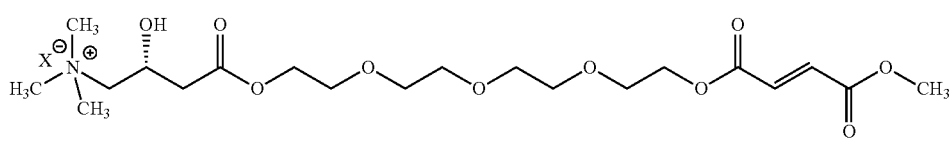

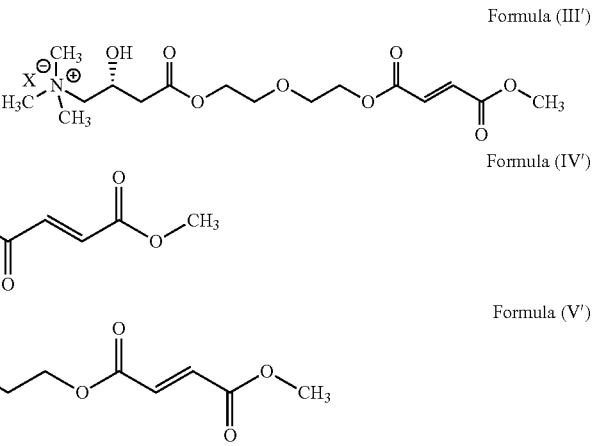

Formula (III')

Formula (IV')

Formula (V')

In a particularly preferred embodiment of the present invention a single compound according to Formula (I') can be used as a medicament.

The same applies to the pharmaceutical composition comprising the compound(s) represented by Formula (I').

Alternatively R' can preferably be —COCH₃. A compound according to Formula (I') with R' being —COCH₃ can be regarded as an (oligo)ethylene glycol wherein one of the hydroxy groups is esterified with MMF and the other hydroxy group is esterified with acetyl carnitine.

In line with the present application acetyl carnitine refers to (R)-acetyl carnitine as well as (S)-acetyl carnitine, preferably (R)-acetyl carnitine.

In a preferred embodiment of the invention in a compound according Formula (I') n' is 1 and R' is —COCH₃.

In an alternatively preferred embodiment of the invention in a compound according Formula (I') n' is 2 and R' is —COCH₃. In a further alternatively preferred embodiment of the invention in a compound according Formula (I') n' is 3 and R' is —COCH₃. In a further alternatively preferred embodiment of the invention in a compound according Formula (I') n' is 4 and R' is —COCH₃.

Thus, in an alternatively especially preferred embodiment the compound according to Formula (I') is selected from the compounds according to Formulae (VI'), (VII'), (VIII') and (IX')

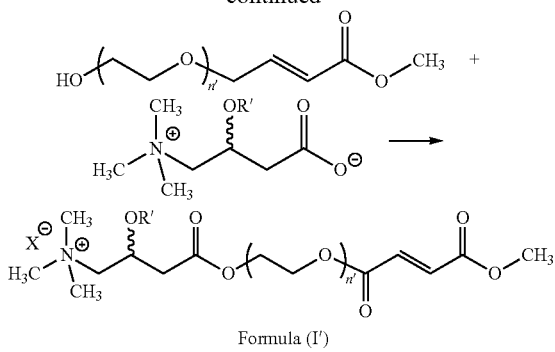

Formula (I')

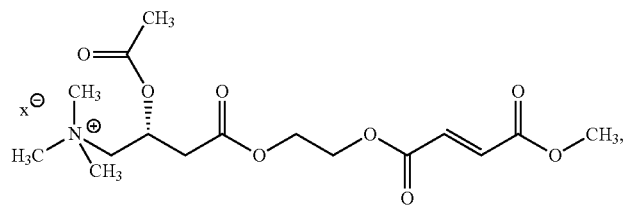

Formula (VI')

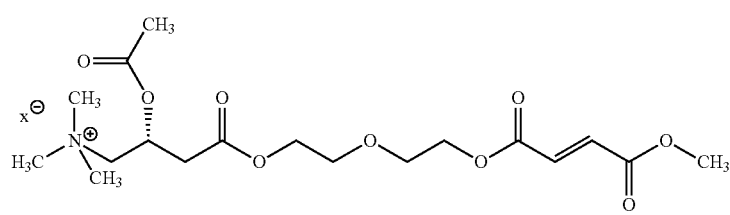

Formula (VII')

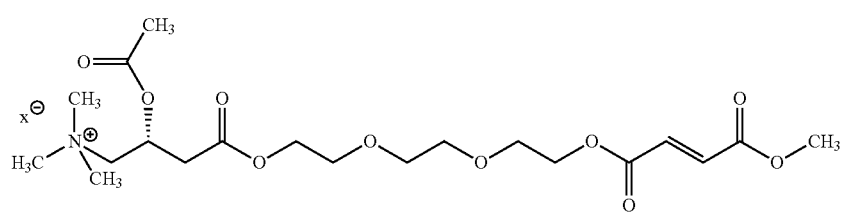

Formula (VIII')

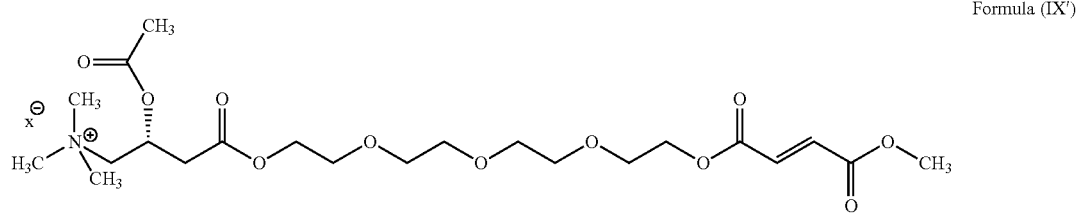

Formula (IX')

A compound according to Formula (I') can preferably be synthesized via the following route:

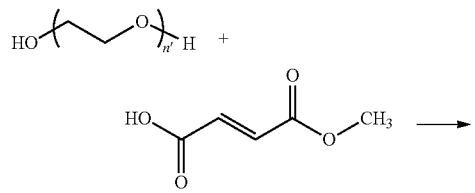

Preferably, in a first reaction step an (oligo)ethylene glycol and MMF can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Suitable coupling agents can be for example DCC (N,N'-dicyclohexylcarbodiimide), DIC (N,N'-diisopropylcarbodiimide), EDC (N-ethyl-N'-(3-methylaminopropyl) carbodiimide hydrochloride), CDI (carbonyldiimidazole), preferably EDC. It is further preferred that the coupling reaction is carried out in the presence of an auxiliary alkaline compound. Suitable alkaline compounds are for example pyridine and amines, such as triethylamine, and diisopropylethylamine and DMAP (4-(dimethylamino)pyridine), in particular DMAP.

A suitable organic solvent can for example be dichloromethane, chloroform, acetonitrile, dioxane, tetrahydrofuran and dimethylformamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with the (oligo)ethylene glycol, preferably in an organic solvent such as dioxane, tetrahydrofuran, chloroform or dichloromethane. Further, the reaction of the acid chloride with the (oligo)ethylene glycol is preferably carried out in the presence of an auxiliary alkaline compound. Suitable alkaline compounds are for example pyridine and amines, such as triethylamine, DMAP (4-(dimethylamino)pyridine) and diisopropylethylamine, preferably triethylamine.

Alternatively, the above acid chloride of MMF can be further transferred in activated esters, like the para-nitrophenol ester.

Further alternatively, MMF can be reacted with acid chlorides, diphenylphosphoryl azide or chlorosulfonyl isocyanate to form (mixed) anhydrides. These (mixed) anhydrides can be also submitted to further reactions to obtain further forms of anhydrides. For example, the anhydride of monomethylfumarate can be obtained by said preparation.

Subsequently, an activated ester or MMF anhydride can be submitted to a reaction with the (oligo)ethylene glycol, preferably in an organic solvent such as dioxane, tetrahydrofuran, chloroform, acetone or dichloromethane. Further, the reaction of an activated ester or MMF anhydride with the (oligo)ethylene glycol is preferably carried out in the presence of an auxiliary alkaline compound. Suitable alkaline compounds are for example pyridine and amines, such as triethylamine, diisopropylethylamine and DMAP (4-(dimethylamino)pyridine), preferably DMAP.

Alternatively, the reaction of the activated ester or MMF anhydride with the (poly)ethylene glycol can preferably be carried out in the absence of an auxiliary alkaline compound. A suitable organic solvent can for example be dioxane, tetrahydrofuran and dimethylformamide.

In a preferred embodiment one of the hydroxy groups of the (oligo)ethylene glycol can be protected with a protection group before being submitted to a reaction with MMF in the presence of a coupling agent or with the acid chloride of MMF or the anhydride of MMF. Such a protection group can for example be a trialkylsilyl group.

After the coupling reaction the protection can preferably be removed by a suitable reaction.

Preferably, in a second reaction step the product from the first reaction step and carnitine or acetyl carnitine can be submitted to an esterification in an organic solvent in the presence of a coupling agent. In the second reaction step preferably the same reaction conditions as in the first reaction step, such as solvent, coupling agent and auxiliary alkaline compound, can be applied.

Further, in case that R' is H, the corresponding hydroxy group of the carnitine residue can be preferably protected with a protection group before being submitted to the esterification with the product from the first reaction step in the presence of a coupling agent or with the acid chloride of MMF or the anhydride of MMF. Such a protection group can for example be a trialkylsilyl group.

After the coupling reaction the protection can preferably be removed by a suitable reaction.

In an alternatively preferred embodiment in a first reaction step carnitine or acetyl carnitine and an (oligo)ethylene glycol can be submitted to an esterification and then the product resulting from that reaction can be preferably submitted with MMF to a further esterification to obtain a product according to Formula (I'). Generally, the same reaction conditions (coupling agent, solvent, optionally alkaline compound, optional protection/deprotection of hydroxy groups) as described above can be applied.

The above-mentioned compounds according to Formula (I') show excellent pharmacokinetic properties. Additionally, the remaining organic residue is not expected to harm the patient's organism.

Further, the present invention relates to the compounds according to Formula (I') for use as a medicament.

A further subject of the invention is the compounds according to Formula (I') for use in the treatment and/or prevention of systemic diseases, autoimmune diseases or inflammatory diseases.

Systemic diseases do not just affect single organs. Instead, these diseases are known to affect a number of organs and tissues or even the body as a whole.

People having an autoimmune disease usually suffer from their immune system mistakenly attacking their own cells of their organism and thus incorrectly responding to substances normally present in the body.

An inflammation can be defined as the response of the body to the occurrence of harmful stimuli which can result in pain, heat, redness, swelling and loss of function of the affected organ.

It is possible that some of the above-mentioned diseases cannot be allocated in one single group of the above-mentioned groups, since they show the symptoms of more than one of them.

In a further preferred embodiment, the compound according to Formula (I') is for use in the treatment of multiple sclerosis, rheumatoid arthritis and psoriasis, preferably multiple sclerosis. The compounds according to Formula (I') can e.g. be used in the treatment of the following types of multiple sclerosis: relapsing-remitting, primary-progressive, secondary-progressive, and progressive-relapsing. In a preferred embodiment the compounds of the present invention are used in the treatment of relapsing-remitting multiple sclerosis.

Further, the present invention also provides a pharmaceutical composition comprising the compound according to the present invention, i.e. a pharmaceutical composition comprising a compound according to Formula (I') and optionally pharmaceutical excipients.

In a preferred embodiment the pharmaceutical composition comprises
(i) 0.01 to 10 mmol, more preferably 0.05 to 5 mmol, still more preferably 0.25 to 3.5 mmol and particularly preferably 0.5 to 2.5 mmol of a compound according to Formula (I');
(ii) pharmaceutical excipient(s).

In a further preferred embodiment the present composition can comprise one or more further excipients, preferably pharmaceutical excipients as described in the European Pharmacopoeia (Ph.Eur.) and/or in the US Pharmacopoeia (USP).

Examples of pharmaceutical excipients are carriers, binders, fillers, disintegrants, wicking agents, glidants and/or lubricants.

In a preferred embodiment the excipients are chosen such that the resulting formulation is a gastric juice-resistant formulation. In a preferred embodiment the formulation of the present invention does not show significant drug release under acidic conditions. In particular, the in-vitro drug release after 2 hours is less than 10%, preferably 0 to 9.9%, more preferably 0 to 5%, still more preferably 0.001 to 3%, measured according to USP, Apparatus II, paddle, 0.1 N HCl, 37° C., 50 rpm.

The pharmaceutical composition can be in a form suitable for oral administration, preferably in the form of a tablet or capsule, in particular in form of a tablet.

It is further preferred that the tablet is coated with a film coating. Alternatively, the capsule could also be coated.

In the present invention, the following three types of film coatings are possible:
film coating without affecting the release of the active ingredient,
gastric juice-resistant film coatings,
retard film coatings.

Generally, film coatings can be prepared by using film-forming agents such as waxes, cellulose derivatives, poly (meth)acrylate, polyvinylpyrrolidone, polyvinyl acetate phthalate, and/or shellac or natural rubbers such as carrageenan.

It is preferred that the present tablet is coated with a gastric juice-resistant film coating. Alternatively, a capsule comprising a gastric juice-resistant film coating can be used.

The gastric juice-resistant film coating preferably is a film coating being stable in the pH range of about 0.7 to 3.0, which is supposed to be the pH-value of human gastric juice found in the stomach. However, in an environment with a pH value of 5 to 9, which is supposed to be present in the (small) intestine of the human body, the gastric juice-resistant film coating preferably dissolves and the drug can be released.

The gastric juice-resistant film coating (often also referred to as enteric coating) can comprise film-forming agents being for example fats, fatty acids, waxes, alginates, shellac, polyvinyl acetate phthalate, cellulose derivatives such as carboxy methyl ethyl cellulose, cellulose acetate succinate, cellulose acetate phthalate, hydroxypropyl methyl cellulose phthalate, hydroxypropyl methyl cellulose acetate succinate, cellulose acetate trimellitate, and meth(acrylic)acid copolymers such as methyl acrylate-methacrylic acid copolymers, methyl methacrylate-methacrylic acid copolymers or Eudragits (for example Eudragit® L30D, Eudragit® L, Eudragit® S).

The coating is preferably free of active ingredient. It is further preferred that the thickness of the coating is usually 10 µm to 2 mm, preferably from 50 to 500 µm.

The preferred coating may comprise a film-forming agent and one or more of the following: lubricant, surfactant, glidant, pigment and water.

The preferred coating according to an embodiment of the present invention can comprise, along with the film-forming agent, e.g. stearic acid as lubricant for plasticizing and dissolving the polymer, sodium lauryl sulfate as a surfactant for wetting and dispersing, talc as glidant, iron oxide yellow and/or titanium oxide as pigment(s) and optionally purified water.

In a preferred embodiment the pharmaceutical composition can be administered one to three times a day, preferably once or twice a day, more preferably once a day.

Further, the present invention relates to a method for treating and/or preventing systemic diseases, autoimmune diseases and/or inflammatory diseases, preferably multiple sclerosis, rheumatoid arthritis or psoriasis, in particular multiple sclerosis, comprising administering to a subject in need thereof a therapeutically effective amount of the compound according to Formula (I') or the pharmaceutical composition of the invention. To the compound according to Formula (I') and the corresponding pharmaceutical composition the same applies as to the compound and the pharmaceutical composition as described above in the text, respectively.

The subjects and preferred embodiments of the second aspect of the present invention can be illustrated by the following items.

1. Compound according to Formula (I')

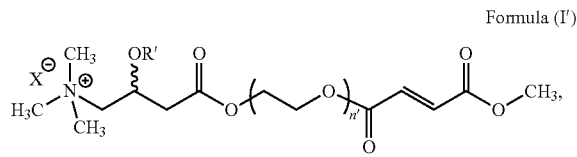

Formula (I')

wherein R' is hydrogen or —COCH$_3$,
n' is an integer from 1 to 10, and
X$^-$ is a pharmaceutically acceptable anion,
or a pharmaceutically acceptable hydrate, solvate, polymorph, and mixtures thereof.

2. Compound according to item 1, wherein in Formula (I') n' is 1, 2, 3 or 4.

3. Compound according to item 1 or 2, wherein in Formula (I') R' is hydrogen.

4. Compound according to any one of item 1 to 3, wherein the compound according to Formula (I') is selected from the compounds according to Formulae (II'), (III'), (IV') and (V')

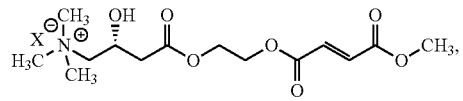

Formula (II')

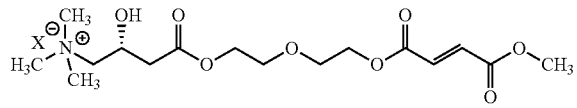

Formula (III')

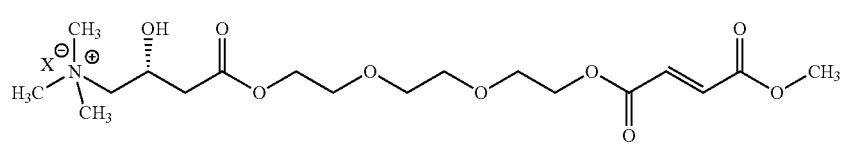

Formula (IV')

Formula (V')

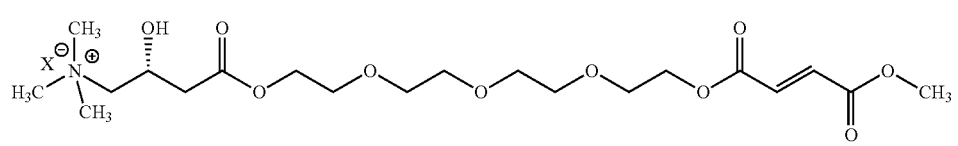

Compound according to item 1 or 2, wherein in Formula (I') R' is COCH$_3$.

6. Compound according to any one of item 1, 2 or 5, wherein the compound according to Formula (I') is selected from the compounds according to Formulae (VI'), (VII'), (VIII') and (IX')

Formula (VI')

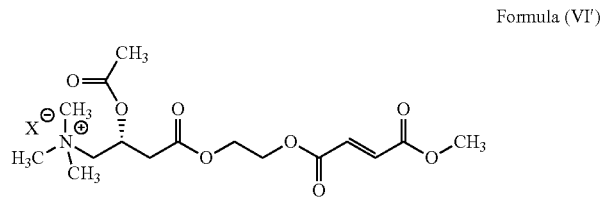

Formula (VII')

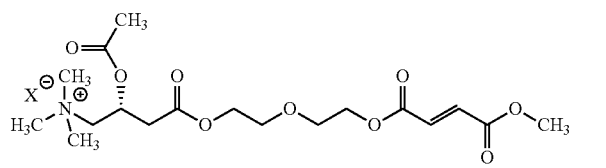

Formula (VIII')

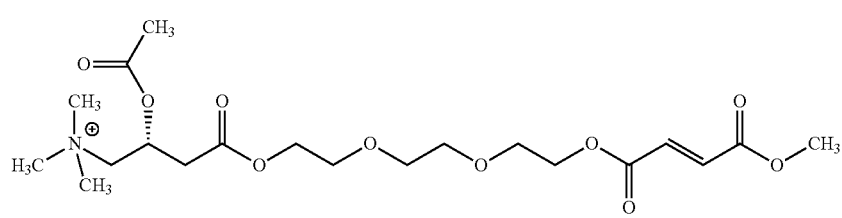

Formula (IX')

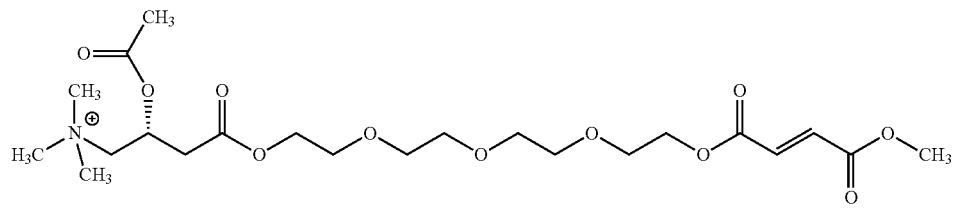

7. Compound according to any one of the preceding items for use as a medicament.
8. Compound according to any one of the preceding items for use in the treatment of systemic diseases, autoimmune diseases or inflammatory diseases, preferably for the use in the treatment of rheumatoid arthritis, multiple sclerosis or psoriasis.
9. Pharmaceutical composition comprising a compound according to any one of the preceding items.
10. Pharmaceutical composition according to item 9, comprising
(i) 0.01 to 10 mmol of a compound according to any one of items 1 to 6 and
(ii) optionally pharmaceutical excipients.

11. Pharmaceutical composition according to item 9 or 10, wherein the composition is a solid oral dosage form.

12. Pharmaceutical composition according to any one of items 9 to 11, wherein the in-vitro drug release after 2 hours is less than 10%, measured according to USP, Apparatus II, paddle, 0.1 HCl, 37° C., 50 rpm.

The invention is illustrated by the following examples.

EXAMPLES

Example 1: (E)-But-2-enedioic acid 2-(2-{2-[2-((E)-3-methoxycarbonyl-acryloyl-oxy)-ethoxy]-ethoxy}-ethoxy)-ethyl ester methyl ester

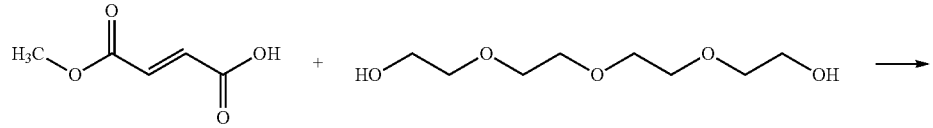

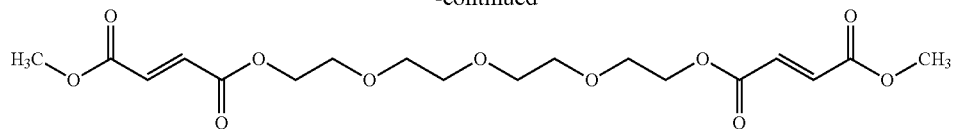

Procedure A:

Tetraethyleneglycol (TEG, 3 g, 15.4 mmol), N-ethyl-N'-(3-methylaminopropyl)carbodiimide hydrochloride (EDC, 8.83 g, 46.3 mmol), and 4-(dimethylamino)pyridine (DMAP, 0.09 g, 0.8 mmol) were suspended in dry THF (30 ml). Monomethylfumarate (4.82 g, 37.1 mmol) was dissolved in THF (50 ml) and added dropwise into the tetraethyleneglycol suspension. The reaction mixture was kept under continuous stirring at 23° C. for 2.5 h. The organic layer was evaporated at 43° C. to yield a syrupy slightly brown product. The crude product was subjected to flash chromatography (eluent: ethyl acetate/n-hexane 4/1 (Rf-value 0.75) to yield the product (4.16 g; 64%) as colourless oil, which was dried under vacuum.

$^1$H NMR (400 MHz, CDCl$_3$) δ ppm 3.65 (s, 8H) 3.74 (t, J=4.69 Hz, 5H) 3.80 (s, 6H) 4.35 (t, J=4.70 Hz, 4H) 6.87 (s, 3H)

$^{13}$C NMR (100 MHz, CDCl$_3$) δ ppm 52.3, 64.4, 68.9, 70.7, 133.5, 164.8, 165.3

Procedure B

Tetraethyleneglycol (TEG, 100 g, 0.51 mol), monomethylfumarate (140.7° g, 1.08 mol) and 4-(dimethylamino)pyridine (DMAP, 6.29° g, 51.5 mmol) were dissolved in dry dichloromethane (1000 ml) at RT. A solution of Dicyclohexylcarbodiimide (DCC, 223.1° g, 1.08 mol) in dichloromethane (300 ml) was added dropwise at 10° C. After the complete addition the reaction mixture was stirred at RT for 0.5 h. The white suspension was filtrated and to the filtrate was added water (1500 ml). The phases were separated and the water layer was extracted twice with dichloromethane (2×750 ml). The combined organic layers were washed with brine (250 ml), dried over sodium sulphate and evaporated. The raw product was dissolved in ethyl acetate (160 ml) at 60° C. and n-hexane was added slowly at this temperature. After the complete addition the mixture was cooled slowly to RT and cooled in fridge for 16 h. The suspension was filtrated and washed with ethyl acetate/n-hexane (1:2) to yield 175.68° g as a yellowish solid. The solid was slurried in diisopropyl ether (750 ml) at RT for 20 h. After that the solid was filtrated and dried in an exsiccator (RT/20 mbar) for 24 h to yield a white solid (155.2 g; 72%).

$^1$H NMR (400 MHz, DMSO-d$_6$) δ ppm 3.53 (s, 8H) 3.64 (t, J=4.70 Hz, 5H) 3.74 (s, 6H) 4.26 (t, J=4.70 Hz, 4H) 6.76 (s, 3H)

Example 2: (E)-But-2-enedioic acid 2-{2-[2-((E)-3-methoxycarbonyl-acryloyl-oxy)-ethoxy]-ethoxy}-ethyl ester methyl ester

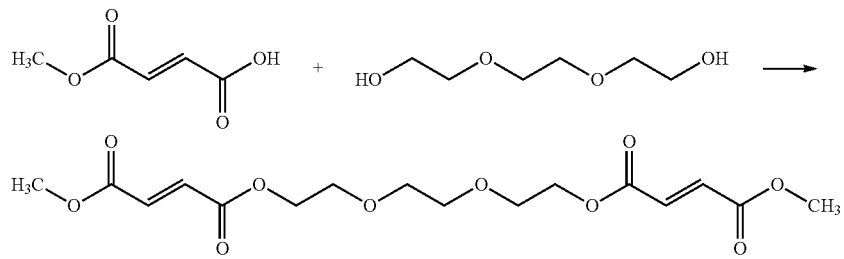

Triethylene glycol (3 g, 20.0 mmol), N-ethyl-N'-(3-methylaminopropyl)carbodiimide hydrochloride (11.49 g, 59.9 mmol), and 4-(dimethylamino)pyridine (0.12 g, 1.0 mmol) were suspended in dry THF (55 ml). Monomethylfumarate (6.24 g, 47.9 mmol) was dissolved in THF (70 ml) and added dropwise into the triethyleneglycol suspension. The reaction mixture was kept under continuous stirring at 23° C. for 2 h. The organic layer was evaporated at 40° C. to yield a syrupy slightly pink/brown product. The crude product was subjected to flash chromatography (eluent: ethylacetate/n-hexane 4/1 (Rf-value 0.7) to yield the product (5.44 g; 73%) as colorless solid, which was dried under vacuum.

$^1$H NMR (400 MHz, CDCl$_3$) δ ppm 3.64 (s, 4H) 3.71-3.76 (m, 4H) 3.77-3.83 (m, 7H) 4.29-4.40 (m, 4H) 6.86 (s, 3H)

$^{13}$C NMR (100 MHz, CDCl$_3$) δ ppm 52.3, 64.4, 68.9, 70.6, 133.4, 133.5, 164.8, 165.3

Example 3: (E)-But-2-enedioic acid 2-[2-((E)-3-methoxycarbonyl-acryloyloxy)-ethoxy]-ethyl ester methyl ester

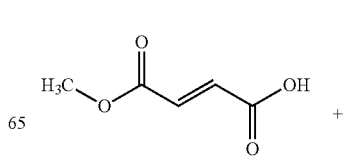

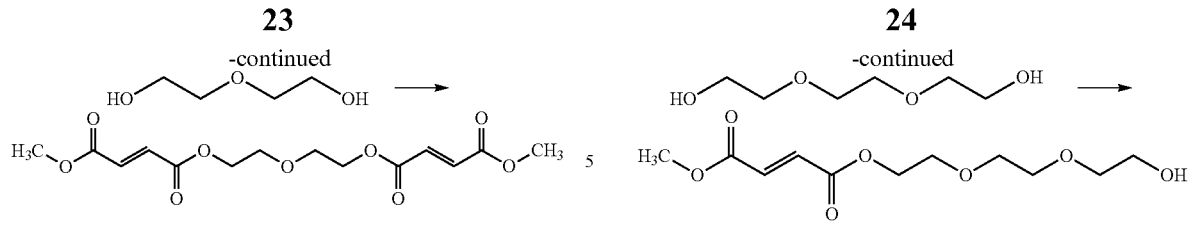

Diethyleneglycol (3 g, 28.3 mmol), N-ethyl-N'-(3-methylaminopropyl)carbodiimide hydrochloride (16.3 g, 84.8 mmol), and 4-(dimethylamino)pyridine (0.17 g, 1.4 mmol) were suspended in dry THF (70 ml). Monomethylfumarate (8.83 g, 67.8 mmol) was dissolved in THF (100 ml) and added dropwise into the diethyleneglycol suspension. The reaction mixture was kept under continuous stirring at 23° C. for 2 h. The organic layer was evaporated at 41° C. to yield a syrupy slightly pink/brown product. The crude product was subjected to flash chromatography (eluent: ethylacetate/n-hexane 4/1 to yield the product (5.9 g; 63%) as colourless solid, which was dried under vacuum.

$^1$H NMR (400 MHz, CDCl$_3$) δ ppm 3.72-3.75 (m, 4H) 3.79 (s, 6H) 4.28-4.40 (m, 4H) 6.86 (s, 4H)

$^{13}$C NMR (100 MHz, CDCl$_3$) δ ppm 52.3, 64.2, 68.8, 133.3, 133.6, 164.8, 165.2

Example 4: (E)-But-2-enedioic acid 2-{2-[2-(2-hydroxy-ethoxy)-ethoxy]-ethoxy}-ethyl ester methyl ester

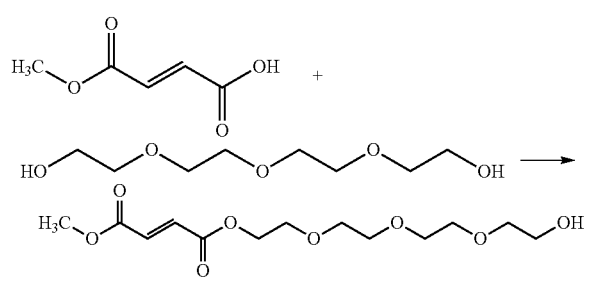

Tetraethyleneglycol (8.96 g, 46.1 mmol), N-ethyl-N'-(3-methylaminopropyl)carbodiimide hydrochloride (3.54 g, 18.4 mmol), and 4-(dimethylamino)pyridine (0.09 g, 0.8 mmol) were dissolved in THF (20 ml). Monomethylfumarate (2 g, 15.4 mmol) was dissolved in THF (30 ml) and added dropwise into the tetraethyleneglycol solution at 23° C. within 20 minutes. The reaction mixture was kept under continuous stirring 23° C. for 1.5 h. Stirring was stopped and a biphasic layer was obtained, the lower layer was discarded and the upper layer evaporated. The obtained crude product was subjected to flash chromatography with 100% ethylacetate or ethylacetate/n-hexane (4/1) to yield the product as colourless oil (2.47 g; 53%).

$^1$H NMR (400 MHz, CDCl$_3$) δ ppm 2.73 (s, 1H) 3.52-3.57 (m, 2H) 3.61 (s, 8H) 3.63-3.73 (m, 4H) 3.75 (s, 3H) 4.26-4.35 (m, 2H) 6.76-6.92 (m, 2H)

Example 5: (E)-But-2-enedioic acid 2-[2-(2-hydroxy-ethoxy)-ethoxy]-ethyl ester methyl ester

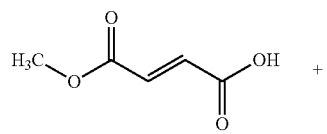

Triethyleneglycol (6.92 g, 46.1 mmol), N-ethyl-N'-(3-methylaminopropyl)carbodiimide hydrochloride (3.54 g, 18.4 mmol) and 4-(dimethylamino)pyridine (0.09 g, 0.8 mmol) were dissolved in THF (20 ml). Monomethylfumarate (2 g, 15.4 mmol) was dissolved in THF (30 ml) and added dropwise into the triethyleneglycol solution at 23° C. within 20 minutes. The reaction mixture was kept under continuous stirring at 23° C. for 1.5 h. Stirring was stopped and a biphasic layer was obtained, the lower layer was discarded and the upper layer evaporated. The obtained crude product was subjected to flash chromatography with 100% ethylacetate or ethylacetate/n-hexane (4/1) to yield the product as colourless oil.

Example 6: (E)-But-2-enedioic acid 2-(2-hydroxy-ethoxy)-ethyl ester methyl ester

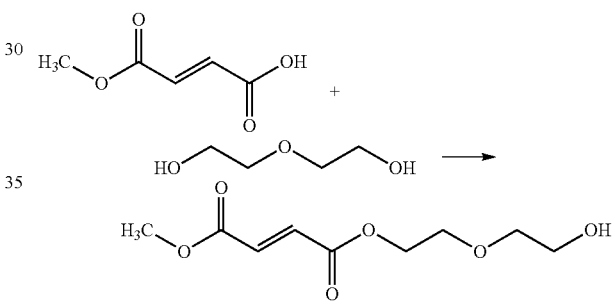

Diethyleneglycol (4.89 g, 46.1 mmol), N-ethyl-N'-(3-methylaminopropyl)carbodiimide hydrochloride (3.54 g, 18.4 mmol) and 4-(dimethylamino)pyridine (0.09 g, 0.8 mmol) were dissolved in THF (20 ml). Monomethylfumarate (2 g, 15.4 mmol) was dissolved in THF (30 ml) and added dropwise into the diethyleneglycol solution at 23° C. within 20 minutes. The reaction mixture was kept under continuous stirring at 23° C. for 1.5 h. Stirring was stopped and a biphasic layer was obtained, the lower layer was discarded and the upper layer evaporated. The obtained crude product was subjected to flash chromatography with 100% ethylacetate or ethylacetate/n-hexane (4/1) to yield the product as colourless oil.

$^1$H NMR (400 MHz, CHLOROFORM-d) δ ppm 2.46 (s, 1H) 3.53-3.59 (m, 2H) 3.69 (s, 4H) 3.75 (s, 3H) 4.31 (m, J=4.70, 4.70 Hz, 2H) 6.82 (s, 2H)

Example 7: Investigation and Comparison of the Kinetics of MMF-Release of the Different Compounds of the Present Invention and DMF During Incubation in Intestinal Fluid of the Minipig 7.1 Material 7.1.1 Test Compounds Compounds of the present invention were synthesized as described above.

7.1.2 Intestinal Fluid

Intestinal tissue/fluid and enterocyte samples were taken from a 10 month old, female Göttingen SPF minipig. The body weight was 21 kg. The minipig was fasted for approximately 28 hours before sampling of intestinal fluid/tissues and enterocytes. On the day of sampling, the minipig was weighed and anaesthetised by an intramuscular injection in the neck or in the left hind leg (about 0.3 ml per kg body weight) of a mixture of Zoletil 50 Vet., Virbac, France (125 mg tiletamine and 125 mg zolazepam), Rompun Vet., Bayer, Germany (20 mg xylazine/ml, 6.5 ml), Ketaminol Vet., Veterinaria AG, Switzerland (100 mg ketamine/ml, 1.5 ml) and Methadon DAK, Nycomed Danmark, Denmark (10 mg methadon/ml, 2.5 ml). The animal was killed by exsanguination before sampling of intestinal fluid. An intestinal segment was ligated at both ends before removal. The isolated tissue was placed in isotonic saline and opened by a longitudinal cut for sampling of intestinal fluid.

The intestinal tissue from each segment was transferred into a Centrifuge Tube, immersed in 10 ml 50 mM phosphate buffer, pH 6.8 and frozen at −70° C.

7.2 Analytical Methods
7.2.1 Quantification of MMF by LC-MS
7.2.1.1 Analytical Instrument Instrument: Acquity UPLC system coupled with a TQ detector (triple quadruple mass spectrometer)
UPLC Method:
Column: Phenomenex Kinetex C18, 100 A, 2.6 μm (150×4.6 mm)
flow: 0.4 ml/min
split: appr. 100 μl/min to MS
Temperature: 30° C.
solvent system (isocratic):
 Solvent A 25% water with 0.1% acetic acid
 Solvent B 75% methanol with 0.1% acetic acid
stoptime: 6 min
autosampler temperature: 8° C.
injection volume: 4 μl
retention time: MN/IF: 4.3 min
 MEF: 4.7 min
Mass Spectrometry
software: Masslynx 4.1
detection mode: electrospray/negative ions (ESP−)
capillary voltage: 2.3 kV
source temperature: 100° C.
desolvation temperature: 450° C.
cone voltage: 18 V
desolvation gas: $N_2$ 650 L/h
cone gas: $N_2$, 20 L/h
collision gas: argon, appr. $3.3*10^{-3}$ mbar
collision energy: 11 eV
MRM [m/z]: 128.94>85.03 Monomethylfumarate dwell: 200 msec
 142.99>99.06 Monoethylfumarate (ISTD) dwell: 200 msec

7.2.1.2 Stock and Calibration Solutions

Stock (SS), working (WS) and calibration solutions of the analyte monomethyl fumarate (MMF) and the internal standard (ISTD) monomethyl fumarate (MEF) were prepared as described below.

$SS_{MMF}$: In a 10 ml volumetric flask, 6.5 mg MMF (Batch: MKRJ0642V/Aldrich) were dissolved in methanol and made up to volume (c=650 μg/ml)

$SS_{ISTD}$: In a 100 ml volumetric flask, 10 mg MEF (Batch: STBC5219V/Aldrich) were dissolved in methanol and made up to volume (c=100 μg/ml)

$WS_{ISTD}$: 100 μl $SS_{ISTD}$ were transferred into a 10 ml volumetric flask and made up to volume with acetonitrile (c=1,000 ng/ml);

Calibration solutions were prepared by serial dilution of $SS_{MMF}$; diluted small intestinal fluid (diluted by 1/20 v/v with 50 mM $KH_2PO_4$, pH 6.8; (dil IF) was used as matrix. The dilution scheme is given below:

| calibration solution | Preparation | | Concentration | |
|---|---|---|---|---|
| | | | [ng/ml] | [μM] |
| cal6500 | 8 μl $SS_{MMF}$ | +792 μl dil IF | 6,500 | 50 |
| cal3250 | 50 μl cal6500 | +50 μl dil IF | 3250 | 25 |
| cal650 | 20 μl cal6500 | +180 μl dil IF | 650 | 5.0 |
| cal325 | 50 μl cal650 | +50 μl dil IF | 325 | 2.5 |
| cal65 | 10 μl cal650 | +90 μl dil IF | 65 | 0.5 |

7.2.1.3 Sample Preparation

50 μl sample (calibration solution or sample of an incubation experiment with MMF prodrugs) was mixed with 50 μl $WS_{ISTD}$, 20 μl formic acid and 100 μl acetonitrile. This mixture was vortexed for 15 sec and centrifuged (13,000 rpm, 3 min). Thereafter, 4 μl of the supernatant were subjected to LC-MS analysis.

7.2.2 Incubation Experiments with DMF (Reference) and Compounds of the Invention
7.2.2.1 Stock Solutions Stock solutions were prepared in DMSO or, for one compound, in DMSO with 10% (v/v) water. Concentrations in stock solutions were 5.00, 2.50 and 1.67 mmol for compounds with one, two and three molar MMF equivalents.

| Compound | MW | Sample weight [mg] | dissolved in | Concentration [mg/ml] | [mmol] |
|---|---|---|---|---|---|
| DMF | 144.13 | 7.21 | 10 ml DMSO | 0.721 | 5.00 |
| Example 1 | 418.40 | 5.29 | 5 ml DMSO | 1.058 | 2.50 |
| Example 2 | 374.35 | 4.68 | 5 ml DMSO | 0.936 | 2.50 |
| Example 3 | 330.29 | 4.13 | 5 ml DMSO | 0.826 | 2.50 |

7.2.2.2 Incubation Experiment

In a HPLC glass vial, 8 μl of stock solution were mixed with 792 μl dil IF and the mixture was stirred (250 rpm) in a water bath (T=37° C.).

Immediately after mixing as well as at t=15 min, 30 min, 60 min, 90 min and 120 min, 50 μl were withdrawn and prepared for LC-MS analysis as described in chapter. 2.1.3.

Incubations were continued and in case the result of analysis of the 120 min indicated the presence of remaining intact MMF prodrug, additional samples were taken (t=360 or 420 min and at 1,260 or 1,320 min) and analysed.

7.3 Results
7.3.1 Calibration of the Analytical Method

Each calibration solution was analysed two-fold. The second analysis was carried out approx. 18 h after storage of the sample in the autosampler, which was cooled to 8° C. The results demonstrate that the ratio of peak area remains essentially unchanged between the first and the second analysis.

The concentration/peak area ratio data pairs were subjected to regression analysis with 1/x weighting and the resulting calibration equation was used to quantify the MMF content in incubation samples.

| calibration standard | nominal concentration [ng/ml] | Analysis | area/ area (ISTD) | mean | RSD |
|---|---|---|---|---|---|
| cal6500 | 6,500 | 1st analysis | 3.569 | 3.567 | 0.07 |
| | | 2nd analysis | 3.564 | | |
| cal3250 | 3,250 | 1st analysis | 1.710 | 1.681 | 1.73 |
| | | 2nd analysis | 1.652 | | |
| cal650 | 650 | 1st analysis | 0.348 | 0.347 | 0.29 |
| | | 2nd analysis | 0.346 | | |
| cal325 | 325 | 1st analysis | 0.174 | 0.169 | 2.96 |
| | | 2nd analysis | 0.164 | | |
| cal65 | 65 | 1st analysis | 0.036 | 0.035 | 2.86 |
| | | 2nd analysis | 0.034 | | |
| cal0 | 0 | 1st analysis | 0.000 | 0.000 | 0.00 |
| | | 2nd analysis | 0.000 | | |

As can be seen from FIG. 1 the inventive compounds according to Examples 1, 2 and 3, which bear two equivalents of MMF, show a modified hydrolyzation than that of DMF. In particular, the release kinetics of the first equivalent of MMF was essentially identical to that of DMF (time 0-30 min) while the second equivalent was released more slowly.

Example 8: In Vivo Pharmacology

Figure 2:
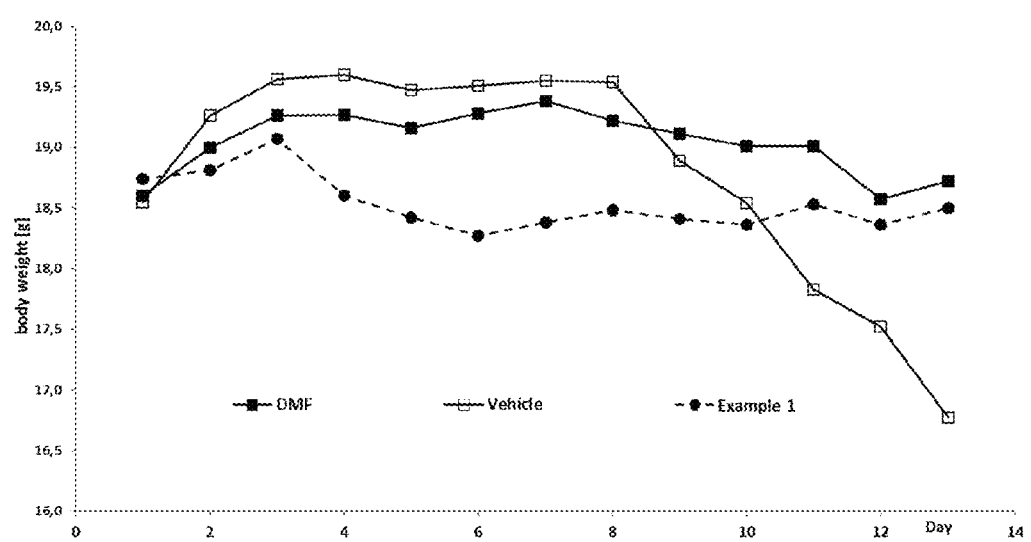
Figure 3:
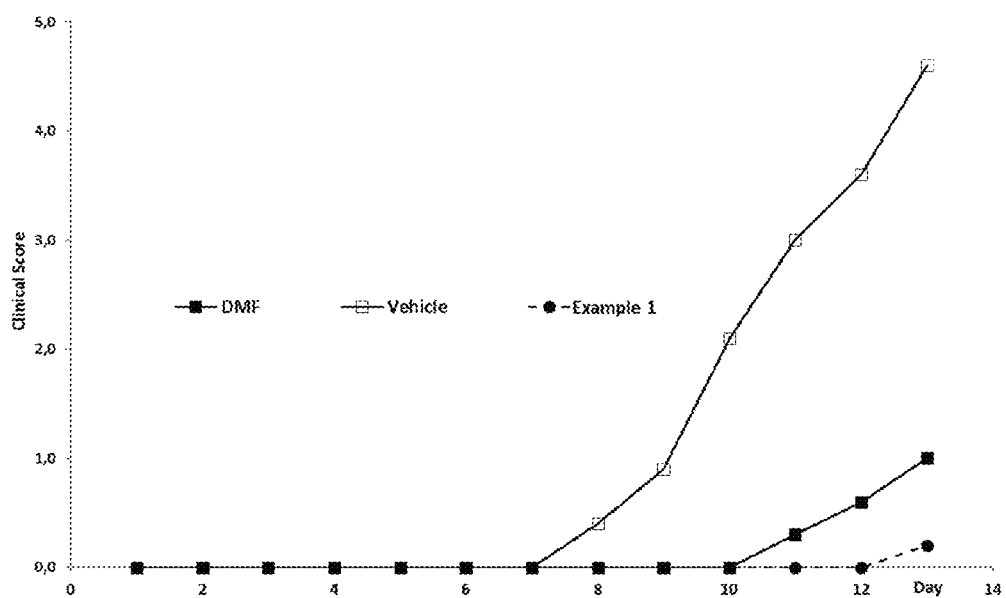

Assessment and comparison of the efficacy of compounds of the invention and DMF (reference) in $MOG_{35-55}$-induced experimental autoimmune encephalomyelitis (EAE) in C57BL/6 mice:
Test system: male C57BL/6 mice, 12 weeks old; 10 animals per treatment group;
Induction of EAE: Day −1—subcutaneous injection of MOG35-55, suspended in complete Freund's adjuvans and intraperitoneal injection of pertussis toxin.
Day 3—intraperitoneal injection of pertussis toxin.
Treatment: Dimethylfumarate and test substances or vehicle only were administered via oral route. Test substances were dissolved or suspended in 0.5% hydroxyethylcellulose (dissolved in 50 mM potassium dihydrogenphosphate, pH 5.0). Drug concentration in dose formulations: 11.54 mM;
Dose volume: 10 ml/kg body weight;
Start of treatment: Day 1
Observations (clinical Observations were recorded daily between day 1 and 13. score and body weight):
Clinical score: grade 0-10; 0 (=no impairments), 1 (normal movement; limp tail: proximal ⅔ of the tail is limp and droopy), 2 (normal movement; whole tail is limp; 3 (wobbly walk; absent righting reflex), 4 (gait ataxia), 5 (mild paraparesis), 6 (moderate paraparesis), 7 (severe paraparesis or paraplegia), 8 (tetraparesis), 9 (moribund), 10 (death).
The results are shown in FIG. 2 (body weight) and FIG. 3 (clinical score). Treatment of animals with vehicle only, first symptoms were observed on day 8 (3 of 10 animals; mean clinical score: 0.4) and the status worsened until day 13 (all animals affected; clinical score: 4.6). In contrast, the prophylactic treatment of animals with DMF or compound of Example 1 protected from the development of clinical symptoms and the body weight remained stable.

Example 9: Membrane Permeability

The membrane permeability was investigated in Caco-2 monolayers. DMF was investigated in a separate experiment for comparison.

Based on the assumption that in vivo, the intact molecules will be pre-systemically metabolized, the permeability test was performed only in the apical→basolateral direction. The test concentration in the apical medium was 250 μM. The assay was validated by controlling the membrane integrity with Lucifer yellow (post-experimental integrity) and by determination of the permeability of atenolol (low permeability), testosterone (high permeability) and erythromycin (P-gp substrate). Furthermore, a significant metabolism or degradation of the test compound was expected and therefore, the parent compound as well as MMF was determined in the acceptor compartment (basolateral medium). Sampling time points were 15, 45 and 90 min.
The results are summarized in the following:

| Item | Direction | $P_{app} \times 10^{-6}$ [cm/sec] mean ± s.d. (CV) | Recovery [%] mean ± s.d. (CV) | Efflux ratio (b-a/a-b) |
|---|---|---|---|---|
| Atenolol | a-b | 0.3 ± 0.1 (45.5%) | 104.1 ± 3.1 (3.0%) | 2.7 |
| | b-a | 0.8 ± 0.2 (23.6%) | 103.3 ± 5.5 (5.3%) | |
| Erythromycin | a-b | 0.1 ± 0.2 (161.8%) | 91.0 ± 1.9 (2.1%) | 100.8 |
| | b-a | 12.3 ± 0.4 (2.9%) | 99.9 ± 2.4 (2.4%) | |
| Testosterone | a-b | 18.2 ± 2.2 (11.9%) | 67.3 ± 1.2 (1.8%) | 2.7 |
| | b-a | 49.5 ± 1.3 (2.7%) | 94.9 ± 0.9 (0.9%) | |
| Example 1 | a-b | 1.0 ± 0.1 (11.1%) | 17.1 ± 0.4 (2.3%) | N/A |
| Atenolol | a-b | 0.3 ± 0.1 (30.0%) | 101.6 ± 3.2 (3.1%) | 2.8 |
| | b-a | 1.0 ± 0.1 (9.2%) | 95.0 ± 5.3 (5.5%) | |
| Erythromycin | a-b | 0.2 ± 0.02 (12.0%) | 107.7 ± 2.2 (2.1%) | 55.9 |
| | b-a | 11.5 ± 0.5 (4.0%) | 89.1 ± 8.5 (9.5%) | |
| Testosterone | a-b | 16.2 ± 1.6 (9.8%) | 62.5 ± 2.1 (3.4%) | 1.9 |
| | b-a | 30.7 ± 1.7 (5.7%) | 76.1 ± 4.5 (6.0%) | |
| DMF | a-b | 1.8 ± 0.2 (12.3%) | 11.6 ± 1.0 (8.2%) | N/A |

The mean apparent permeability of the test compounds expressed as $P_{app} \times 10^{-6}$ is 1.8±0.2 cm/sec was for DMF and 1.0±0.1 cm/sec for Example 1. Compared to the reference molecules, DMF and the compound of Example 1 can be categorized as moderate permeability drugs. The recovery of all test and reference compounds was similar (11.6% for DMF, 17.1% for compound of Example 1), which indicates a similar susceptibility to hydrolysis.

Example 10: In Vivo Pharmacokinetics

Figure 4:
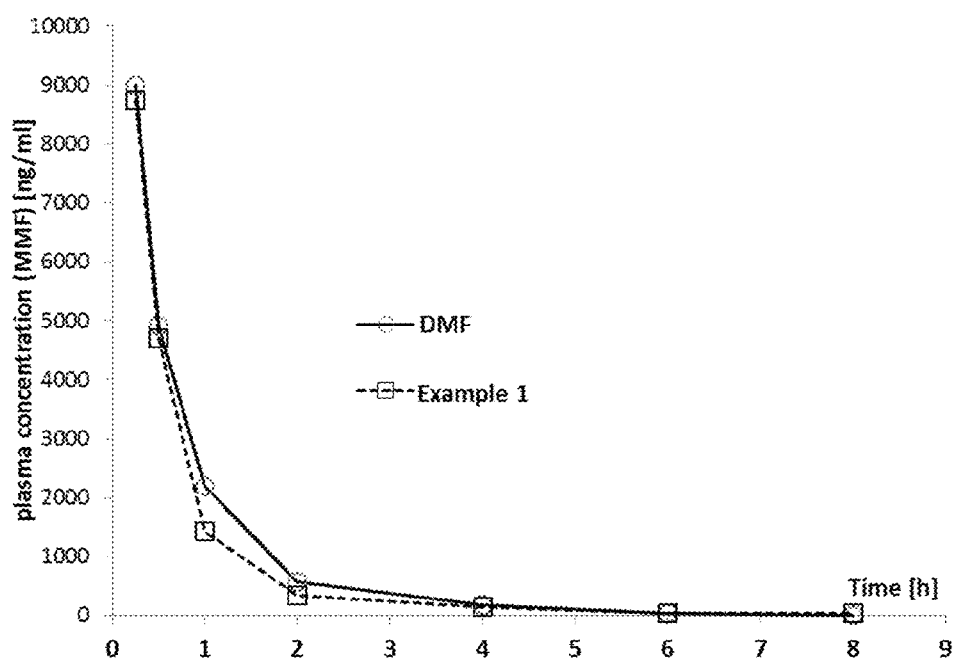
Figure 5:
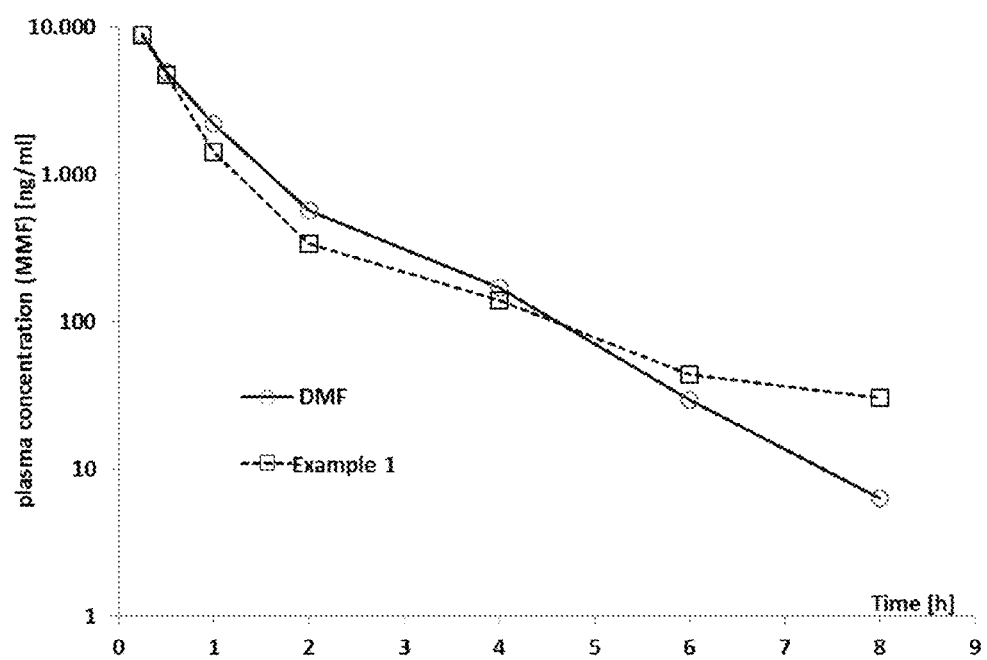

The pharmacokinetics of MMF after administration of the compound of Example 1 and DMF for comparison was investigated in female NMRI mice (3 animals per group). The test compound was dissolved in DMSO/PEG300 (20/80) and administered p.o. (gavage) at a dose volume of 10 ml/kg. DMF was given at a dose of 45 mg/kg. The test compound was dosed at a MMF-equivalent dose, i.e. 65.3 mg/kg. Blood samples were taken at 0.25, 0.5, 1.0, 2.0, 4.0, 6.0 and 8.0 h after drug administration.
Mean concentration vs. time profiles of MMF in the linear and semi-logarithmic scale are shown in FIG. 4 and FIG. 5.

Pharmacokinetic parameters, derived by non-compartmental analysis for test compound (Example 1):

| animal no. | $C_{max}$ [ng/ml] | $T_{max}$ [h] | $AUC_{last}$ [ng * h/ml] | $t_{1/2}$ [h] | $AUC_{inf}$ [ng * h/ml] | $AUC_{\% Extrap}$ [%] | F* [%] |
|---|---|---|---|---|---|---|---|
| 1 | 6,860 | 0.25 | 5,120 | 0.49 | 5,140 | 0.36 | 73.1 |
| 2 | 6,700 | 0.25 | 6,040 | 1.02 | 6,080 | 0.69 | 86.5 |
| 3 | 12,700 | 0.25 | 6,550 | 1.56 | 6,750 | 3.03 | 96.0 |
| mean: | 8.753 | 0.25 | 5.903 | 1.02 | 5.990 | 1.36 | 85 |
| s.d.: | 3.419 | 0.00 | 725 | 0.54 | 809 | 1.45 | 12 |
| C.V.: | 39% | 0% | 12% | 52% | 14% | 107% | 14% |

*F = bioavailability of MMF relative to administration of DMF and of DMF for comparison:

| animal no. | $C_{max}$ [ng/ml] | $T_{max}$ [h] | $AUC_{last}$ [ng * h/ml] | $t_{1/2}$ [h] | $AUC_{inf}$ [ng * h/ml] | $AUC_{\% Extrap}$ [%] | F [%] |
|---|---|---|---|---|---|---|---|
| 4 | 13,000 | 0.25 | 6,750 | 1.13 | 6,800 | 0.79 | N/A |
| 5 | 7,330 | 0.25 | 7,630 | 2.83 | 7,710 | 1.00 | N/A |
| 6 | 6,640 | 0.25 | 6,530 | 0.96 | 6,580 | 0.81 | N/A |
| mean: | 8,990 | 0.25 | 6,970 | 1.64 | 7,030 | 0.87 | N/A |
| s.d.: | 3,490 | 0.00 | 582 | 1.03 | 599 | 0.12 | N/A |
| C.V.: | 39% | 0% | 8% | 63% | 9% | 14% | N/A |

The rate and extent of systemic exposure of animals to MMF after administration of the different compounds were very similar. Compared to the bioavailability of MMF after administration of DMF, the relative bioavailability of MMF after administration of test compound (Example 1) was 85%.

Example 11: Effect of MMF-Prodrugs According to Example 1 and Example 2 on Imiquimod-Induced Psoriasis-Like Skin Inflammation BALB/c mice (n=6 per treatment group), 8 to 10 weeks old, received a daily topical dose of 65 mg of commercially available IMQ cream (5%) (Aldara; 3M Pharmaceuticals) on the shaved back for 8 consecutive days (day 1 to day 8).

The test articles (Example 1 and Example 2) were administered via the oral route twice daily between day 5 and day 8 at a dose of 15 mg/kg. For administration of the compound according to Example 1, the solid compound was dissolved in 0.5% hydroxyethylcellulose (in 50 mM $KH_2PO_4$, pH 5.0) at a concentration of 2.18 mg/ml. For administration of the compound according to Example 2, 1 vol. of a stock solution (19.5 mg/ml in DMSO) was dissolved with 9 vol. of 0.5% hydroxyethylcellulose (in 50 mM $KH_2PO_4$, pH 5.0). The dose volume was 10 ml/kg.

The effect of treatment with vehicle only, with intravenously administered anti-TNF antibody (=positive control) or with the test articles was evaluated on day 9. The severity of inflammation of the back skin was determined using the PASI (psoriasis area and severity index) scoring system as follows: 0=normal mouse skin; 1=mild reddening; 2=erythema; 3=erythema, swelling; 4=erythema, swelling, scaling; 5=erythema, swelling, scaling, (bloody) lesions.

Furthermore, cytokines (IFN-γ, TNF-α and IL-27) and chemokines (IP-10 and GRO-α) were determined in serum from blood samples, which were withdrawn on day 9.

Figure 6:
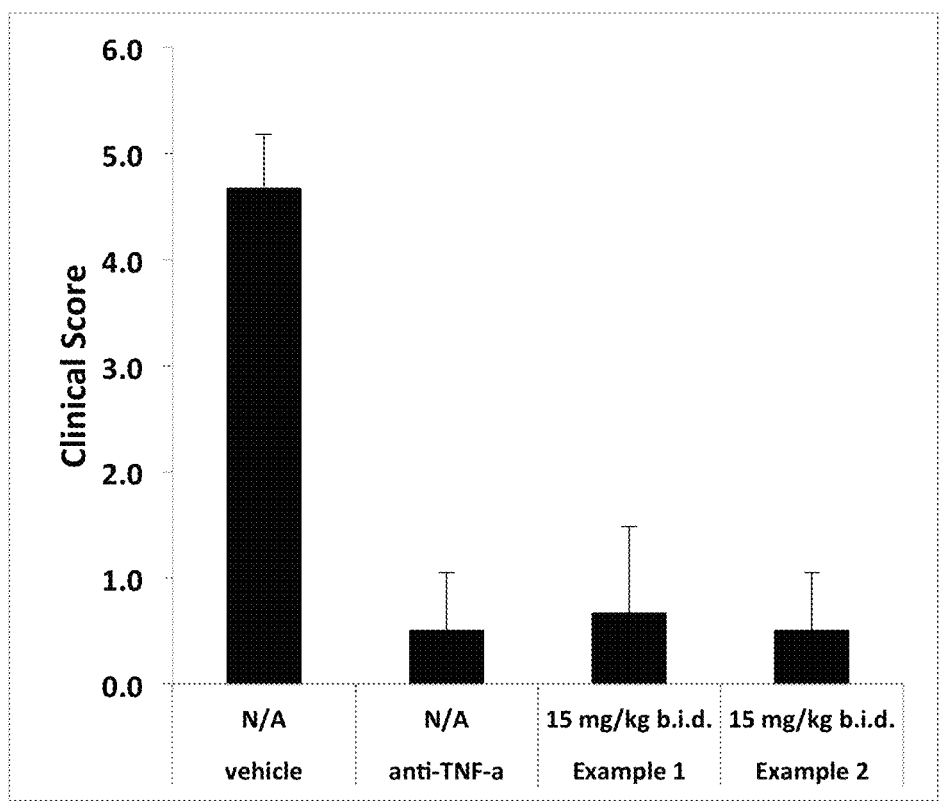

In FIG. 6 the effect of treatment with vehicle (p.o., twice daily), anti-TNFa antibody (i.v., two injections in total), as well as test substances (according to Example 1 and Example 2, p.o. twice daily, 15 mg/kg) on the PASI score in Imiquimod-induced psoriasis in Balb/c mice is shown.

Figure 7A:
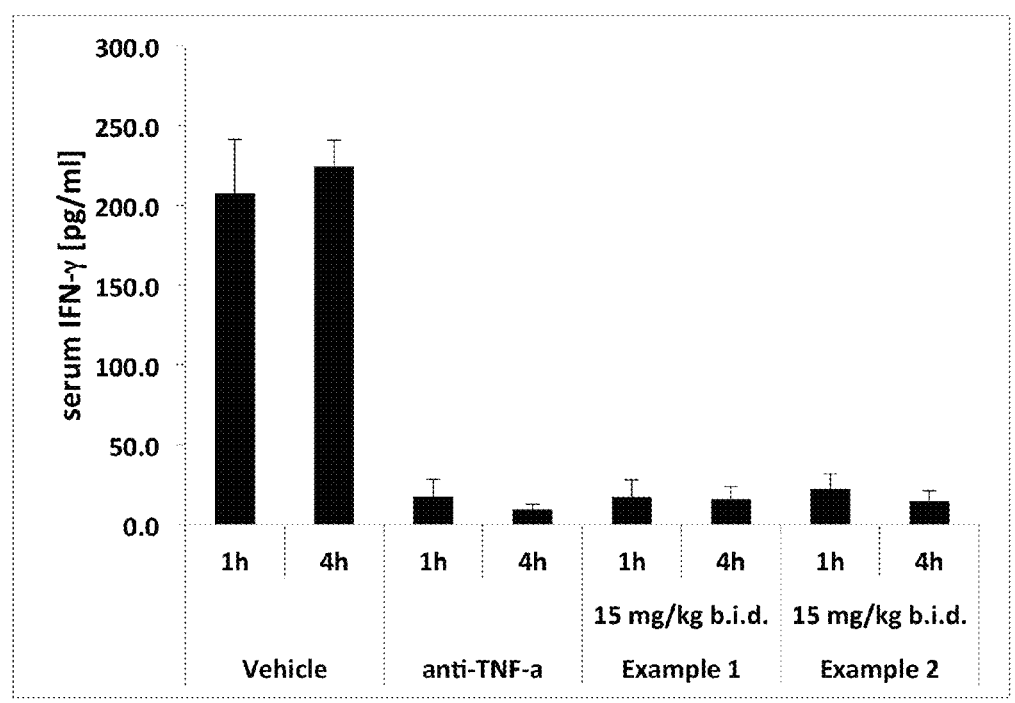
Figure 7B:
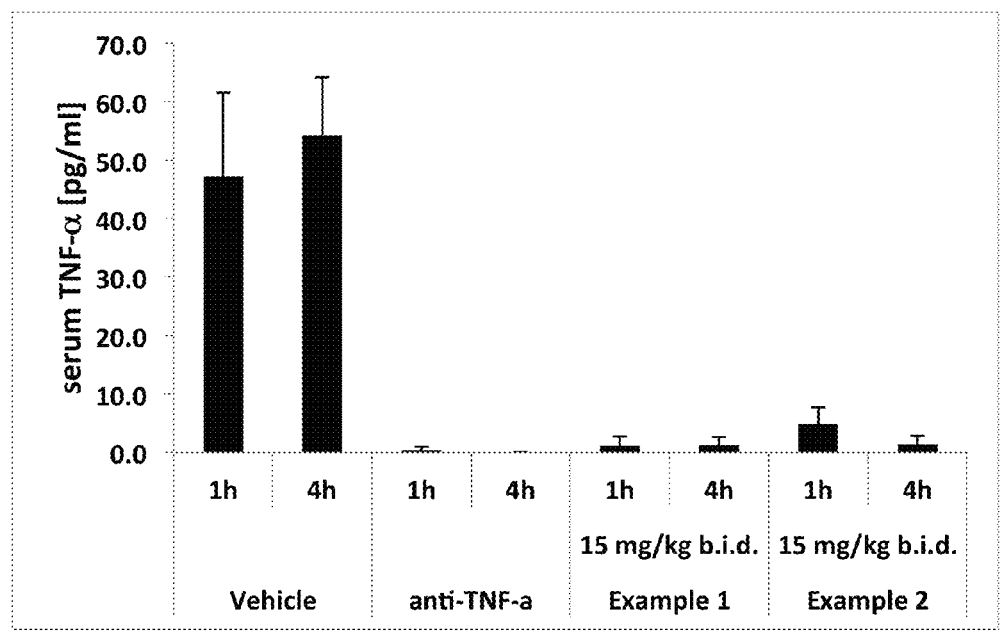
Figure 7C:
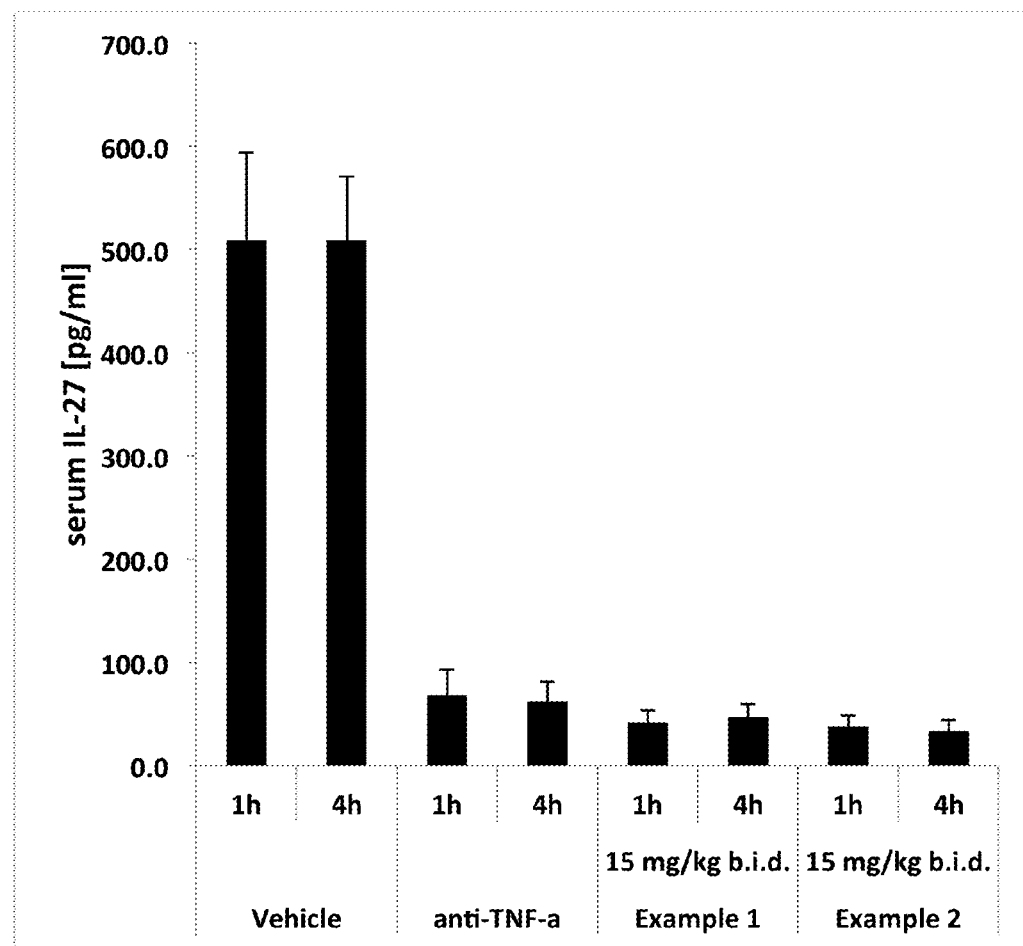
Figure 7D:
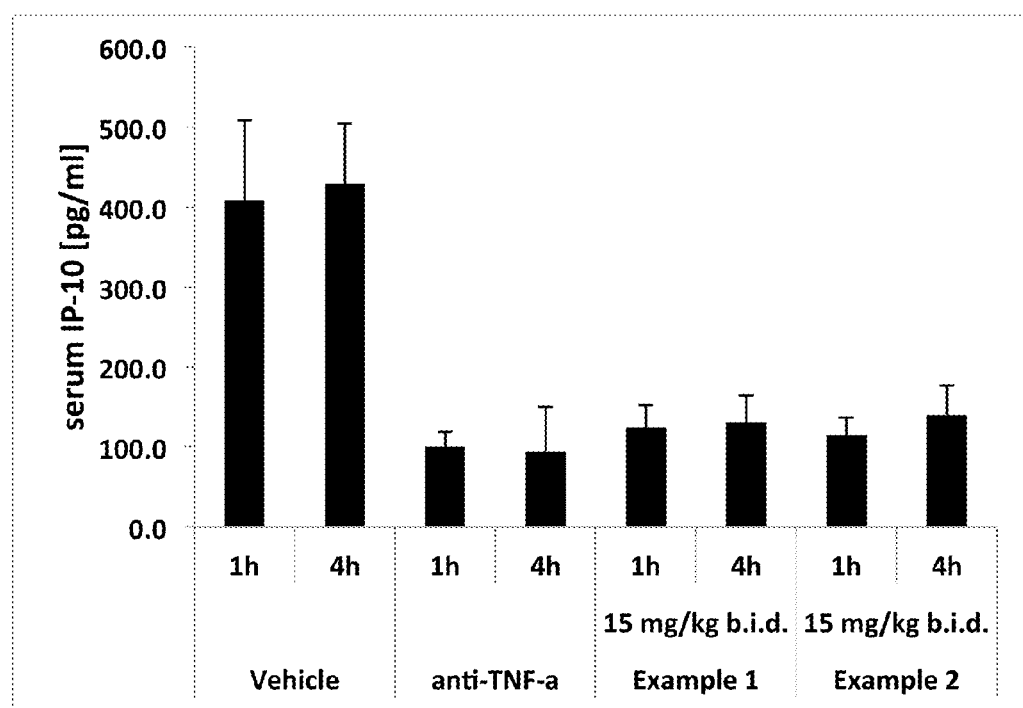
Figure 7E:
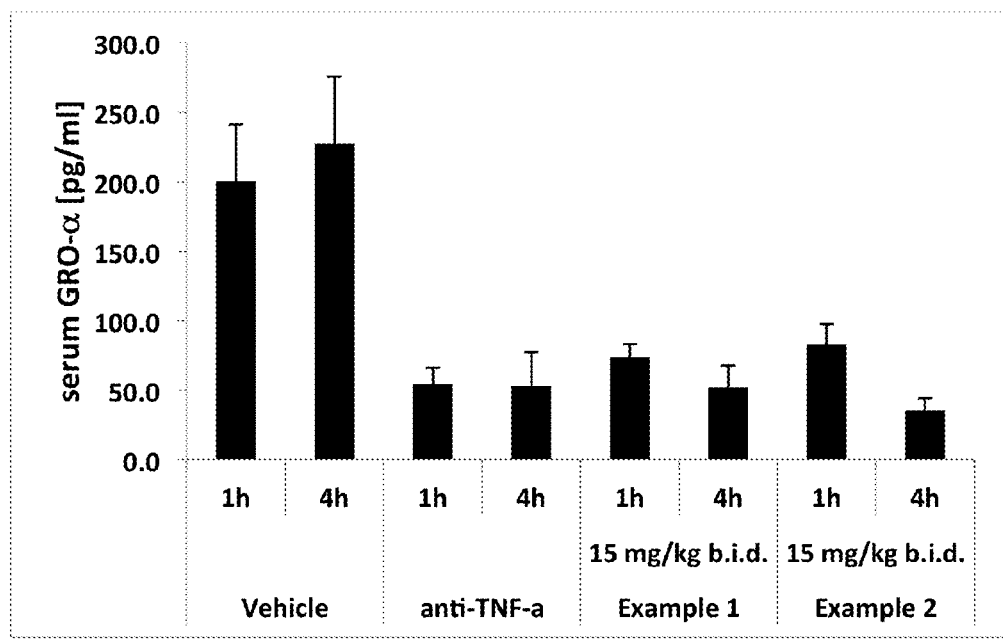

In FIGS. 7a through 7e the effect of treatment with vehicle (p.o., twice daily), anti TNFa antibody (i.v., two injections in total), as well as test substances (according to Example 1 and Example 2, p.o. twice daily, 15 mg/kg) on the serum cytokine and chemokine concentrations (FIG. 7a (IFN-γ), 7b (TNF-α), 7c (IL-27), 7d (IP-10) and 7e (GRO-α) in Imiquimod-induced psoriasis in Balb/c mice. Blood samples were withdrawn 1 h and 4 h after the final treatment is presented.

Reference Example: Comparison of the Kinetics of MMF-Release of (E)-but-2-enedioic acid 1-((e)-3-methoxycarbonyl-acryloyloxy)-ethyl ester methyl ester According to Example 45 of WO2010022177 (US20100048651) and DMF During Incubation in Intestinal Fluid of the Minipig (E)-But-2-enedioic acid 1-chloro-ethyl ester methyl ester Anhydrous zinc chloride (0.1 g; 0.8 mmol) was added to pure (E)-3-Chlorocarbonyl-acrylic acid methyl ester (5.6 g; 38 mmol) and the resulting mixture stirred for 2 h at room temperature. Acetaldehyde (2.5 mL; 45 mmol) was added dropwise while maintaining the temperature below 20° C. After complete addition stirring was continued for 1 h and after quenched with water (15 mL) and aqueous NaHCO3 (10%; 6 mL). The mixture was extracted with EtOAc (2×100 mL), the combined organic layers washed with brine (50 mL), dried over Na2SO4 and concentrated under reduced pressure. The remaining crude product was purified via silica gel chromatography (eluent: 10:1 v/v; n-heptane: MtBE) to yield 1.7 g (8.8 mmol; 23%) of pure (E)-But-2-enedioic acid 1-chloro-ethyl ester methyl ester.

(E)-But-2-enedioic acid 1-((E)-3-methoxycarbonyl-acryloyloxy)-ethyl ester methyl ester A solution of mono-Methyl fumarate (1.72 g; 13.2 mmol) in N-Methylpyrrolidone (10 mL) was added to pure (E)-But-2-enedioic acid 1-chloro-ethyl ester methyl ester (1.7 g; 8.8 mmol) followed by NaHCO3 (0.96 g; 11.5 mmol). The resulting suspension was heated to 55° C. and stirred for 4 h. Due to a moderate conversion, the reaction temperature was increased to 80° C. and stirring was continued for 12 h. The mixture was allowed to reach room temperature, diluted with ethyl acetate (150 mL) and washed with water (2×50 mL) and brine (50 mL). The organic layer was dried over Na2SO4, concentrated under reduced pressure and the remaining crude product purified via silica gel chromatography (eluent: 4:1 v/v; n-heptane: MtBE) to yield 0.79 g (2.8 mmol; 31%) of a colorless solid.

Figure 8:
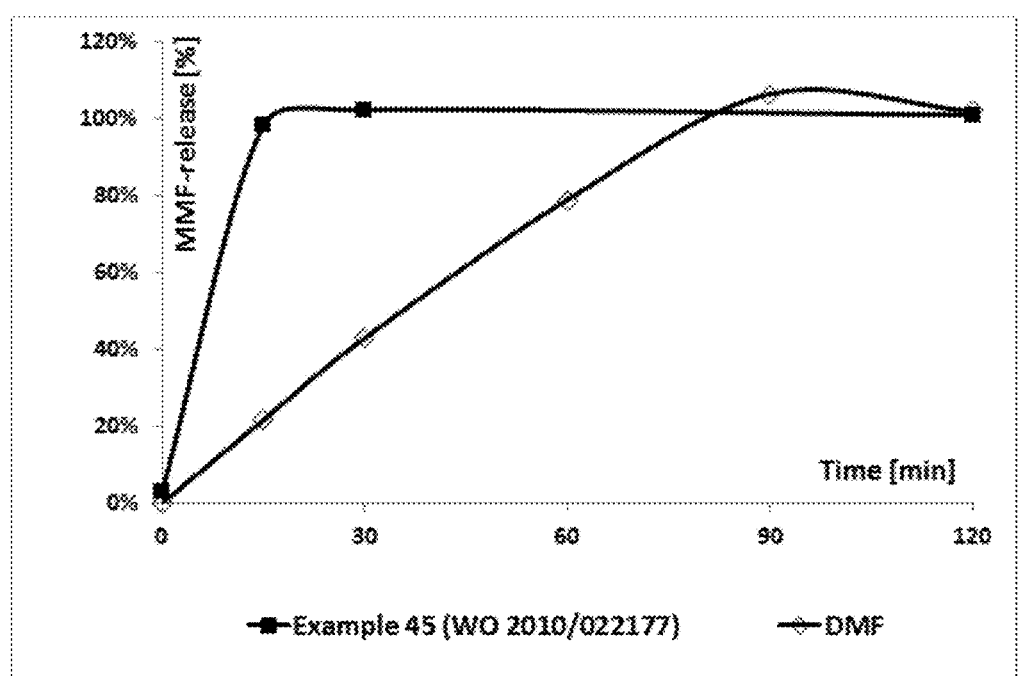

As can be seen from FIG. 8 (E)-But-2-enedioic acid 1-((E)-3-methoxycarbonyl-acryloyloxy)-ethyl ester methyl ester, which bears one equivalents of MMF, show a different hydrolyzation than that of DMF. In particular, the release kinetics is considerable faster than that of DMF.

The invention claimed is:

1. A compound according to Formula (I)

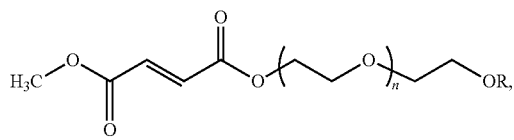

Formula (I)

wherein
R is hydrogen and n is an integer from 1 to 10, or
R is trans —CO—CH═CH—COOCH₃ and n is an integer from 2 to 10,
or a pharmaceutically acceptable salt, hydrate, solvate, polymorph, and/or mixtures thereof.

2. The compound according to claim 1, wherein R is hydrogen and n is 1, 2 or 3.

3. The compound according to claim 1, selected from the group consisting of compounds according to Formulae (II), (III) and (IV):

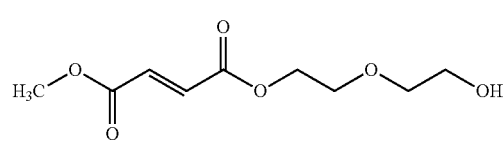

Formula (II)

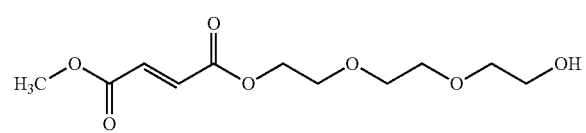

Formula (III)

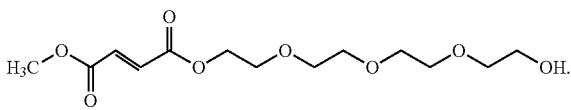

Formula (IV)

4. The compound according to claim 1, wherein R is trans —CO—CH═CH—COOCH₃.

5. The compound claim 1, selected from the group consisting of compounds according to Formulae (VI) and (VII):

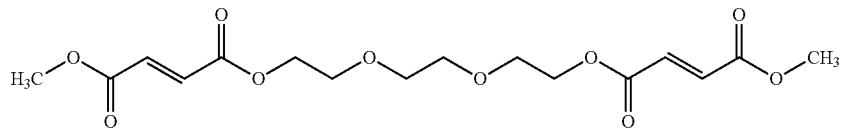

Formula (VI)

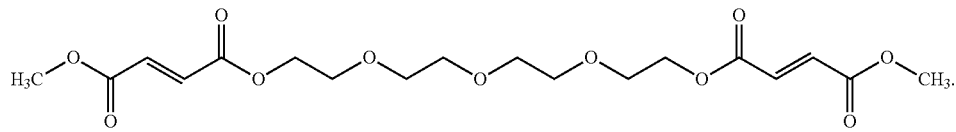

Formula (VII)

6. A method for treating a disease, comprising administering to a subject in need thereof a therapeutically effective amount of a pharmaceutical composition comprising
a compound according to claim 1, and
one or more pharmaceutical excipients,
wherein the disease is elected from the group consisting of systemic diseases, autoimmune diseases and inflammatory diseases.

7. The method according to claim 6, wherein n is 1, 2 or 3.

8. The method according to claim 6, wherein R is hydrogen.

9. The method according to claim 6, wherein the compound is selected from the group consisting of compounds according to Formulae (II), (III) and (IV):

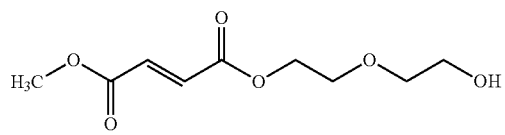

Formula (II)

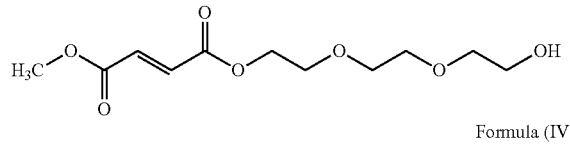

Formula (III)

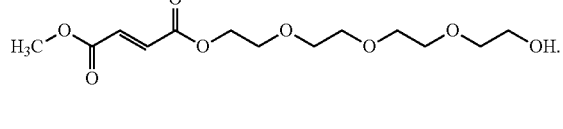

Formula (IV)

10. The method according to claim 6, wherein R is trans —CO—CH═CH—COOCH₃.

11. The method according to claim 6, wherein the compound is selected from the group consisting of compounds according to Formulae (VI) and (VII):

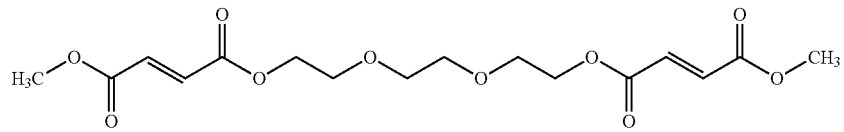

Formula (VI)

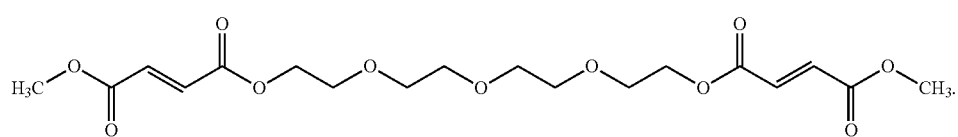

Formula (VII)

12. The method according to claim 6, wherein the disease is selected from the group consisting of multiple sclerosis, rheumatoid arthritis and psoriasis.

13. A pharmaceutical composition comprising a compound according to claim 1 and one or more pharmaceutical excipients.

14. The pharmaceutical composition according to claim 13, comprising 0.01 to 10 mmol of the compound.

15. The pharmaceutical composition according to claim 13, wherein the pharmaceutical composition is a solid oral dosage form.

16. The pharmaceutical composition according to claim 13, wherein the in-vitro drug release after 2 hours is less than 10%, measured according to USP, Apparatus II, paddle, 0.1 HCl, 37° C., and 50 rpm.

17. The method according to claim 12, wherein the disease is multiple sclerosis.

* * * * *